United States Patent
White et al.

[11] Patent Number: 6,099,558
[45] Date of Patent: Aug. 8, 2000

[54] INTRALUMINAL GRAFTING OF A BIFURICATED ARTERY

[75] Inventors: Geoffrey H. White, East Balmain; Weiyun Yu, Five Dock, both of Australia

[73] Assignee: Edwards Lifesciences Corp., Irvine, Calif.

[21] Appl. No.: 09/068,587

[22] PCT Filed: Nov. 10, 1996

[86] PCT No.: PCT/AU96/00713

§ 371 Date: Jan. 25, 1999

§ 102(e) Date: Jan. 25, 1999

[87] PCT Pub. No.: WO97/17910

PCT Pub. Date: May 22, 1997

[30] Foreign Application Priority Data

Oct. 10, 1995 [AU] Australia .................................. PN6513
Nov. 10, 1995 [AU] Australia .................................. PN6512
Nov. 10, 1995 [AU] Australia .................................. PN6514

[51] Int. Cl.$^7$ ........................................................ A61F 2/06
[52] U.S. Cl. ........................ 623/1.16; 623/1.13; 623/1.35
[58] Field of Search ................................ 623/1, 12, 1.16, 623/1.13, 1.35; 606/198, 195; 128/898

[56] References Cited

U.S. PATENT DOCUMENTS

| | | |
|---|---|---|
| 4,149,911 | 4/1979 | Clabburn . |
| 4,225,979 | 10/1980 | Rey et al. . |
| 4,306,318 | 12/1981 | Mano et al. . |
| 4,512,338 | 4/1985 | Balko et al. . |
| 4,553,545 | 11/1985 | Maass et al. . |
| 4,617,932 | 10/1986 | Kornberg . |
| 4,649,922 | 3/1987 | Wiktor . |
| 4,665,906 | 5/1987 | Jervis . |
| 4,665,918 | 5/1987 | Garza et al. . |
| 4,681,110 | 7/1987 | Wiktor . |
| 4,728,328 | 3/1988 | Hughes et al. . |
| 4,729,766 | 3/1988 | Bergentz et al. . |
| 4,732,152 | 3/1988 | Wallsten et al. . |
| 4,762,128 | 8/1988 | Rosenbluth . |

(List continued on next page.)

FOREIGN PATENT DOCUMENTS

| | | |
|---|---|---|
| 0177300 | 3/1986 | European Pat. Off. . |
| 0335341 | 10/1989 | European Pat. Off. . |
| 0421729 | 4/1991 | European Pat. Off. . |
| 0686379A2 | 12/1995 | European Pat. Off. . |
| 0792627A3 | 11/1997 | European Pat. Off. . |
| 2409747 | 10/1980 | France . |
| 2512678 | 11/1985 | France . |
| 2189150 | 10/1987 | United Kingdom . |
| WO83/00997 | 3/1983 | WIPO . |
| WO90/04982 | 5/1990 | WIPO . |
| WO92/0004 | 1/1992 | WIPO . |
| WO95/08966 | 4/1995 | WIPO . |
| WO 96/11648 | 4/1996 | WIPO . |
| WO96/10375 | 4/1996 | WIPO . |
| WO96/28116 | 9/1996 | WIPO . |

*Primary Examiner*—Michael J. Milano
*Assistant Examiner*—Hieu Phan
*Attorney, Agent, or Firm*—Edwards Lifesciences LLC; Peter Jon Gluck; B. M. Canter

[57] ABSTRACT

A method for positioning an intraluminal graft within a branching vessel in a patient's body is described. The method is particularly applicable to the appropriate positioning of a trouser graft so that it bridges an aneurism which extends from a single vessel, such as the aorta, into one or more divergent vessels, for example, an iliac artery. The method can comprise the steps a of placing a first graft (10), that bifurcates in a pair of tubular sections (19a, 19b) into the pre-branching portion of a vessel (11) through one of the post-branching portions of the vessel (12, 13), positioning a second tubular graft (10b) into one of the post-branching portions (12) and connecting it to one of the tubular sections of the first graft (19a), and positioning a third tubular graft (10a) into the other of the post-branching portions (11) and connecting it to the other of the tubular sections of the first graft (19b).

24 Claims, 17 Drawing Sheets

U.S. PATENT DOCUMENTS

| | | |
|---|---|---|
| 4,772,264 | 9/1988 | Cragg . |
| 4,800,882 | 1/1989 | Gianturco . |
| 4,820,298 | 4/1989 | Leveen et al. . |
| 4,878,906 | 11/1989 | Lindemann et al. . |
| 4,886,062 | 12/1989 | Wiktor . |
| 4,886,065 | 12/1989 | Collins, Jr. . |
| 4,913,141 | 4/1990 | Hillstead . |
| 4,969,458 | 11/1990 | Wiktor . |
| 4,969,890 | 11/1990 | Sugita et al. . |
| 4,994,071 | 2/1991 | MacGregor . |
| 5,019,090 | 5/1991 | Pinchuk . |
| 5,037,427 | 8/1991 | Harada et al. . |
| 5,047,050 | 9/1991 | Arpesani . |
| 5,057,092 | 10/1991 | Webster, Jr. . |
| 5,064,435 | 11/1991 | Porter . |
| 5,067,957 | 11/1991 | Jervis . |
| 5,078,726 | 1/1992 | Kreamer . |
| 5,078,736 | 1/1992 | Behl . |
| 5,085,635 | 2/1992 | Cragg . |
| 5,104,404 | 4/1992 | Wolff . |
| 5,133,732 | 7/1992 | Wiktor . |
| 5,183,085 | 2/1993 | Timmermans . |
| 5,192,297 | 3/1993 | Hull . |
| 5,201,901 | 4/1993 | Harada et al. . |
| 5,207,695 | 5/1993 | Trout, III . |
| 5,236,446 | 8/1993 | Dumon . |
| 5,275,622 | 1/1994 | Lazarus et al. . |
| 5,342,387 | 8/1994 | Summers . |
| 5,354,309 | 10/1994 | Schnepp-Pesch et al. . |
| 5,366,504 | 11/1994 | Anderson et al. . |
| 5,383,928 | 1/1995 | Scott et al. . |
| 5,387,235 | 2/1995 | Chuter . |
| 5,397,345 | 3/1995 | Lazarus . |
| 5,415,664 | 5/1995 | Pinchuk . |
| 5,429,144 | 7/1995 | Wilk . |
| 5,443,496 | 8/1995 | Schwartz et al. . |
| 5,443,497 | 8/1995 | Venbrux ........................................ 623/1 |
| 5,443,498 | 8/1995 | Fontaine . |
| 5,456,713 | 10/1995 | Chuter . |
| 5,464,449 | 11/1995 | Ryan et al. . |
| 5,489,295 | 2/1996 | Piplani et al. ............................... 623/1 |
| 5,507,767 | 4/1996 | Maeda et al. . |
| 5,507,771 | 4/1996 | Gianturco . |
| 5,522,880 | 6/1996 | Barone et al. ............................... 623/1 |
| 5,562,724 | 10/1996 | Vorwerk et al. . |
| 5,562,726 | 10/1996 | Chuter ........................................ 623/1 |
| 5,562,727 | 10/1996 | Turk et al. . |
| 5,562,728 | 10/1996 | Lazarus et al. . |
| 5,571,170 | 11/1996 | Palmaz et al. . |
| 5,575,817 | 11/1996 | Martin . |
| 5,609,605 | 3/1997 | Marshall et al. ........................ 606/191 |
| 5,609,627 | 3/1997 | Goicoechea et al. ...................... 623/1 |
| 5,676,696 | 10/1997 | Marcade ...................................... 623/1 |
| 5,676,697 | 10/1997 | McDonald ................................... 623/1 |
| 5,683,449 | 11/1997 | Marcade ...................................... 623/1 |
| 5,683,450 | 11/1997 | Goicoechea et al. . |
| 5,683,451 | 11/1997 | Lenker et al. . |
| 5,683,453 | 11/1997 | Palmaz ........................................ 623/1 |
| 5,693,086 | 12/1997 | Goicoechea et al. . |
| 5,709,713 | 1/1998 | Evans et al. . |
| 5,716,365 | 2/1998 | Goicoechea et al. . |
| 5,718,724 | 2/1998 | Goicoechea et al. . |
| 5,720,776 | 2/1998 | Chuter et al. ............................... 623/1 |
| 5,752,522 | 5/1998 | Murphy . |
| 5,782,904 | 7/1998 | White et al. ................................. 623/1 |
| 5,797,949 | 8/1998 | Parodi ...................................... 606/194 |
| 5,824,039 | 10/1998 | Piplani et al. ............................... 623/1 |
| 5,824,040 | 10/1998 | Cox et al. ................................... 623/1 |
| 5,824,055 | 10/1998 | Spiridigliozzi et al. .................... 623/1 |
| 5,860,923 | 1/1999 | Lenker et al. . |
| 5,871,536 | 2/1999 | Lazarus ....................................... 623/1 |
| 5,938,696 | 8/1999 | Goicoechea et al. ........................ 623/1 |

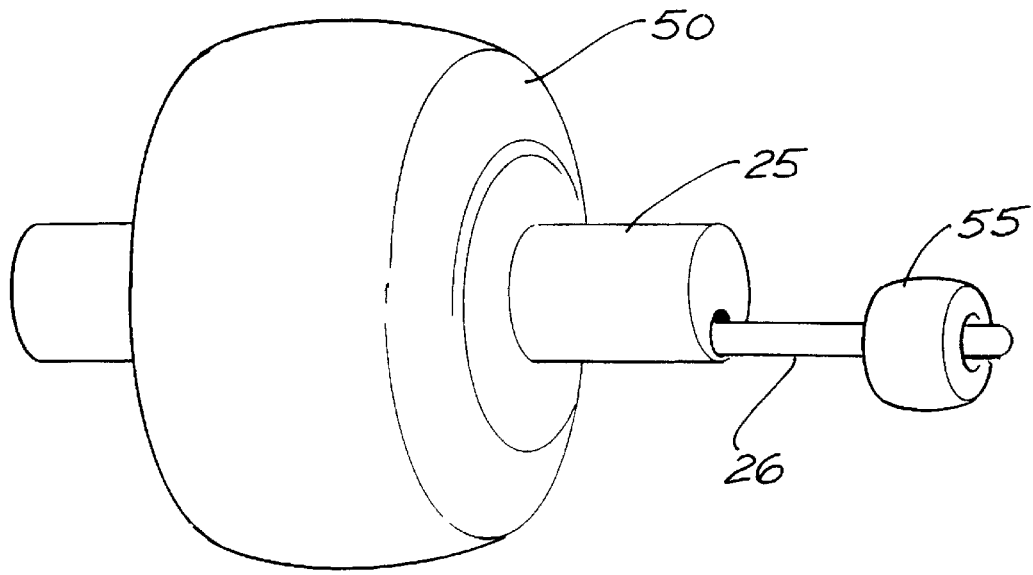
FIG. 6b
FIG. 6c
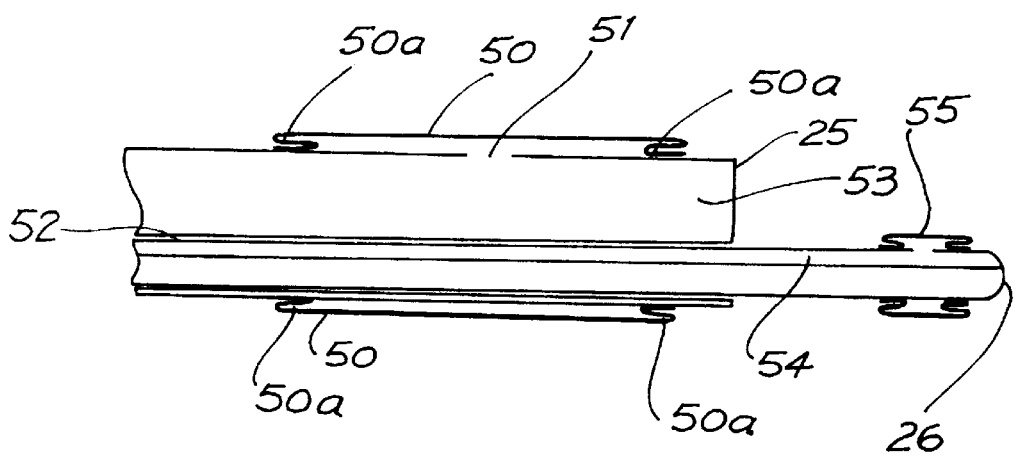

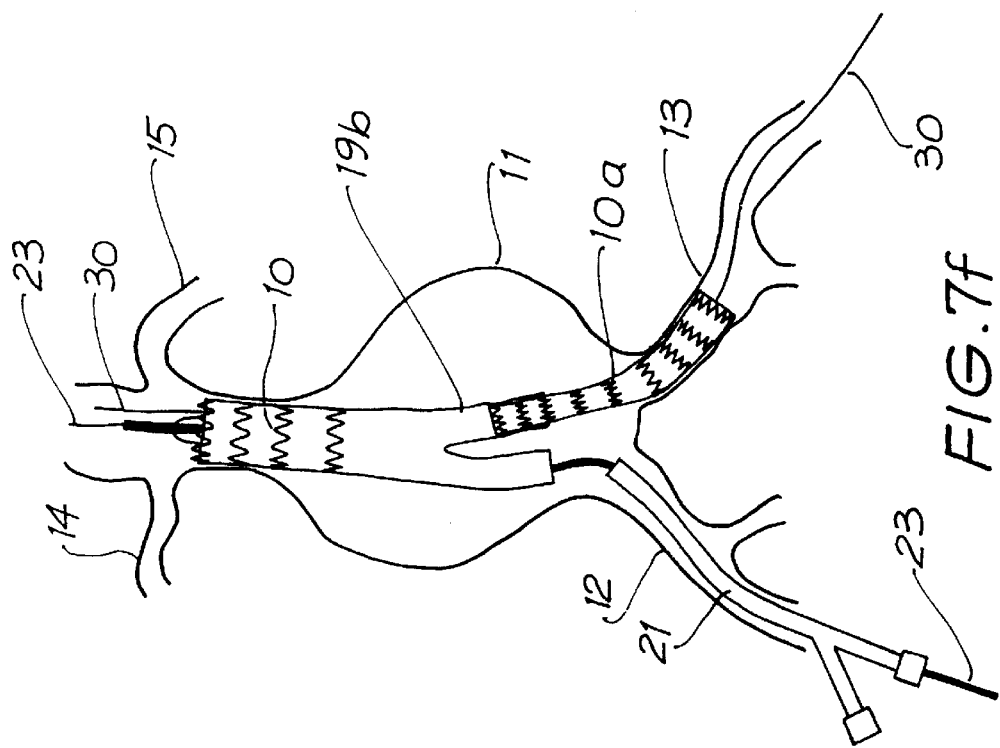
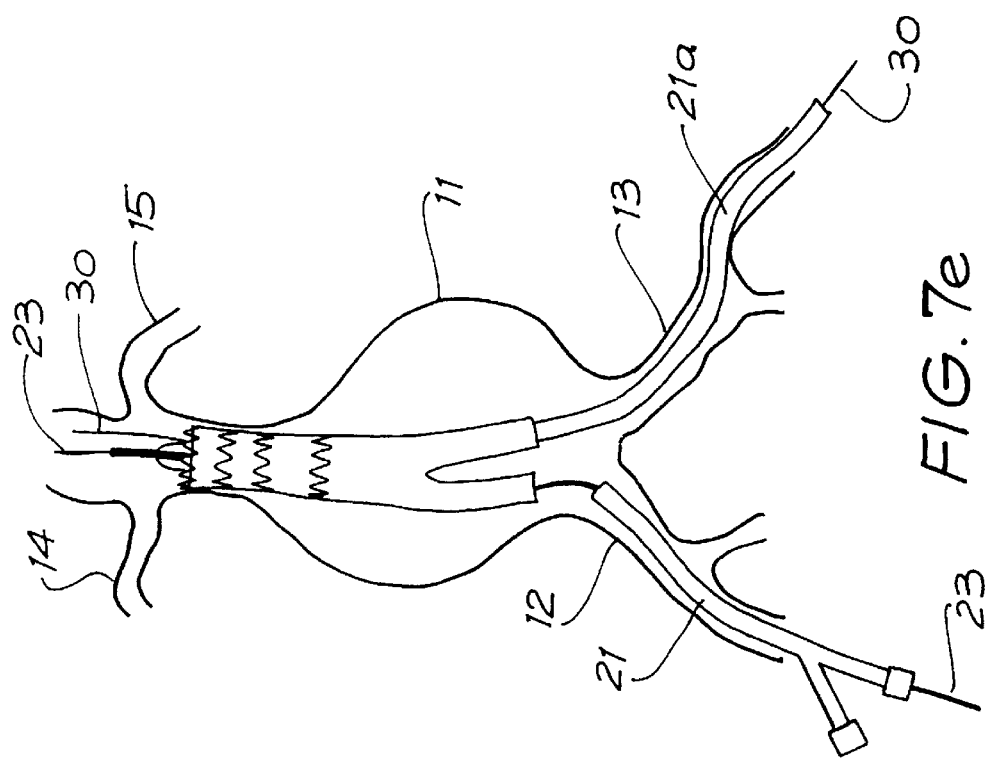
FIG. 7f
FIG. 7e

INTRALUMINAL GRAFTING OF A BIFURICATED ARTERY

FIELD OF THE INVENTION

The present invention relates to a method for positioning all intraluminal graft into a bifurcating vessel such as an artery.

BACKGROUND ART

It is well known that through disease, arteries of humans are susceptible to the development of distended sacs known as aneurysms which are susceptible to rupture. Traditionally, aneurysms are treated by radical surgical graft replacement. This approach is risky for the patient and is, in many cases, not feasible due to other pre-existing disease states in the patient. More recently there have been a number of proposals for the intraluminal placement of an intraluminal graft bridging the aneurysms and thereby isolating an active arterial duct from the aneurysmal sac. One such arrangement is described in Australian Patent Application No. 78035/94.

Difficulties arise in the placement of such intraluminal grafts when the aneurysm extends from a single artery into one or more divergent arteries. In this case a so called "trouser graft" must be used. In such a graft a single tubular body bifurcates in a downstream direction into two smaller tubular bodies. The intention being that the single tubular body is placed in the single artery and the two smaller tubular bodies are respectively placed in the two divergent arteries (see, for example, U.S. Pat. No. 5,360,443 to Barone). In practice it has proven very difficult to effectively place a trouser graft.

DISCLOSURE OF THE INVENTION

According to a first aspect, the present invention consists in a method for positioning an intraluminal graft in a branching vessel within a patient's body, the vessel comprising a single pre-branching vessel branching into a pair of post-branching vessels, the method comprising:

(a) introducing a first intraluminal graft wholly within the pre-branching vessel through one of the post-branching vessels, the first intraluminal graft having a body having, at a first end, a tubular portion that is expandable into contact with a circumferential wall of the pre-branching vessel, and at a second end a bifurcation into first and second tubular graft extensions;

(b) introducing a second intraluminal graft comprising an expandable tubular body, having an upstream end and a downstream end, into one of the post-branching vessels, moving the second graft until its upstream end is within, or surrounds, one of the tubular graft extensions of the first intraluminal graft and its downstream end is within the one of the post-branching vessels and causing the tubular body of the second intraluminal graft to form fluid conveying engagement with that tubular graft extension and with that vessel; and (c) introducing a third intraluminal graft comprising an expandable tubular body, having an upstream end and a downstream end, into the other of the post-branching vessels, moving the third graft until its upstream end is within, or surrounds, the other of the tubular graft extensions of the first intraluminal graft and its downstream end is within the other of the post-branching vessels and causing the tubular body of the third intraluminal graft to form fluid conveying engagement with that tubular graft extension and with that vessel.

In a preferred embodiment of this aspect of the invention the first intraluminal graft is introduced through a first one of the post-branching vessels and the second intraluminal graft is introduced through the other of the post-branching vessels. The third intraluminal graft is then introduced through the first one of the post-branching vessels.

Instead of placing the bifurcated graft first it is possible to place one of the "leg" grafts first and to then position the bifurcated graft. Thus, in a second aspect, the invention consists in a method for positioning an intraluminal graft in a branching vessel within a patient's body comprising a single pre-branch vessel branching into a pair of post-branching vessels, the method comprising:

(a) introducing a first intraluminal graft comprising an expandable tubular body, having an upstream end and a downstream end, into one of the post-branching vessels and expanding its downstream end into contact with that vessel;

(b) introducing a second intraluminal graft into the other of the post-branching vessels until it is positioned wholly within the pre-branching vessel, the second intraluminal graft having a body, having at a first end, a tubular portion that is expandable into contact with a circumferential wall of the pre-branching vessel, and at a second end a bifurcation into first and second tubular graft extensions, expanding the first end of the second graft into contact with the wall of the pre-branching vessel and causing one of the tubular graft extensions to form fluid conveying engagement with the first intraluminal graft; and (c) introducing a third intraluminal graft comprising an expandable tubular body, having an upstream end and a downstream end, into the other of the post-branching vessels, moving the third intraluminal graft until its upstream end is within, or surrounds, the other of the tubular graft extensions of the second intraluminal graft and its downstream end is within the other of the post-branching vessels and causing the tubular body of the third intraluminal graft to form fluid conveying engagement with that tubular graft extension and with that vessel.

In a still further aspect, the present invention consists in a method for positioning an intraluminal graft in a branching vessel within a patient's body comprising a single pre-branching vessel branching into a pair of post-branching vessels, the method comprising:

(a) introducing a first intraluminal graft comprising an expandable tubular body, having an upstream end and a downstream end, into one of the post-branching vessels and expanding at least its downstream end into contact with that vessel;

(b) introducing a second intraluminal graft into the one post-branching vessel, the second intraluminal graft having a body, having at a first end, a tubular portion that is expandable into contact with a circumferential wall of the pre-branching vessel, and at a second end a bifurcation into first and second tubular graft extensions, with one tubular graft extension having a greater length than the other tubular graft extension, and passing the second intraluminal graft through the first intraluminal graft until its first end is in the pre-branching vessel and the other tubular graft extension has cleared the first intraluminal graft, expanding the first end of the second graft into contact with the wall of the pre-branching vessel and causing the one tubular graft extension to form fluid conveying attachment with the first intraluminal graft; and (c) introducing a third intraluminal graft comprising an expandable tubular body, having an upstream end and a downstream end, into the other of the post-branching vessels, moving the third graft until its upstream end is within, or surrounds, the other tubular graft extension of the second intraluminal graft and its downstream end is within the other post-branching vessel and causing the tubular portion of the third intraluminal graft to form fluid conveying engagement with that tubular graft extension and with that vessel.

In each of the above aspects, the method can further comprise the following step of:

(d) introducing a further intraluminal graft comprising an expandable tubular body, having an upstream end and a downstream end, into the one and/or other post-branching vessel, moving the further graft until its upstream end is within the downstream end of the intraluminal graft in the post-branching vessel and causing the tubular body of the further intraluminal graft to form fluid conveying engagement with the downstream end of the graft in the post-branching vessel and with the surrounding post-branching vessel.

In one embodiment of the further aspects, the step of positioning the first intraluminal graft in one of the post-branching vessels in turn can comprise the steps of:

(a) guiding a first fine guidewire through the one post-branching vessel and preferably at least into the pre-branching vessel;

(b) guiding a first fine catheter sheath over the first fine guidewire until it at least enters the pre-branching vessel;

(c) withdrawing the first fine guidewire;

(d) inserting a second relatively stiff guidewire through the first fine catheter sheath until it at least enters the pre-branching vessel;

(e) withdrawing the first fine catheter sheath;

(f) guiding a second relatively larger diameter catheter sheath over the second guidewire until it at least enters the pre-branching vessel;

(g) guiding a first delivery catheter, which has an uninflated balloon adjacent a first end and the downstream end of the first intraluminal graft disposed about the balloon, over the second guidewire and within the second larger diameter catheter sheath;

(h) positioning the first delivery catheter so that the first graft is in the post-branching vessel;

(i) partially withdrawing the second catheter sheath to free the first intraluminal graft; and (j) inflating the balloon and so expanding the downstream end of the first intraluminal graft until it engages against the post-branching vessel wall.

The invention according to the present invention is typically used where a single vessel branches into two vessels such as the aorta branching into the iliac arteries. It could also be used where there are a plurality of vessels branching from a single vessel such as occurs in the aortic arch.

In a particularly preferred embodiment of the above aspects of the present invention, the intraluminal grafts have the features of the grafts described in Australian Patent Application No. 78035/94 the contents whereof are incorporated herein by reference.

The present invention is hereinafter described with reference to the placement of a trouser graft in a bifurcating artery which is a typical application. The method according to the present invention could, however, be used to place a trouser graft in any branching vessel in the body. Such vessels include, in addition to arteries, veins, trachea and tracheoles and bile ducts.

While the tubular bodies of the grafts used in carrying out the invention are expandable, as by a balloon catheter, at least one of the tubular sections of the first intraluminal graft may be formed with self expanding stents. Such stents may act to hold the tubular sections to receive the tubular bodies of the second and third intraluminal grafts.

It is preferred that the intraluminal graft is of such a length that each of the tubular graft extensions terminates upstream of the bifurcation in the artery. In this arrangement a separate tubular graft is used to link each tubular extension with its associated distal artery. In an alternative arrangement the intraluminal graft includes one tubular extension long enough to project into the first of the distal arteries. In this case the other tubular extension terminate above the bifurcation and a second, tubular, graft joins that extension with the second distal artery.

BRIEF DESCRIPTION OF THE DRAWINGS

FIG. 6b is an enlarged view of the inflatable balloons adjacent respectively the free end of a catheter and guidewire, with the balloons inflated;

FIG. 6c is a longitudinal sectional view of the device of FIG. 6b with the balloons uninflated;

FIGS. 7a to 7i show the stages of carrying out one method according to the present invention;

PREFERRED MODE OF CARRYING OUT THE INVENTION

Figure 1:
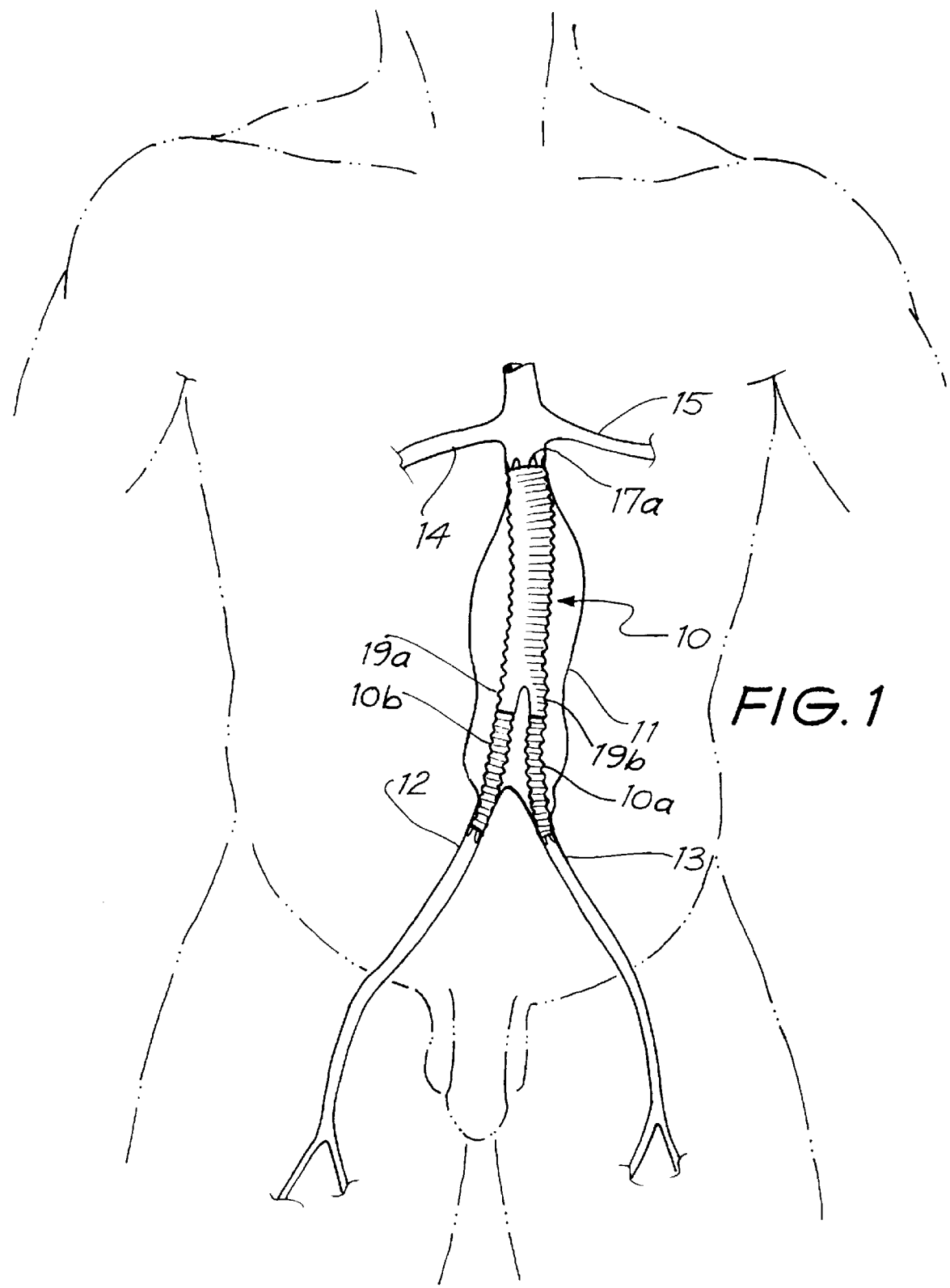
FIG. 1 is a diagrammatic partially cut-away central view of a patient with an aortic aneurysm which has been bridged by an intraluminal graft according to the present invention.
Figure 2:
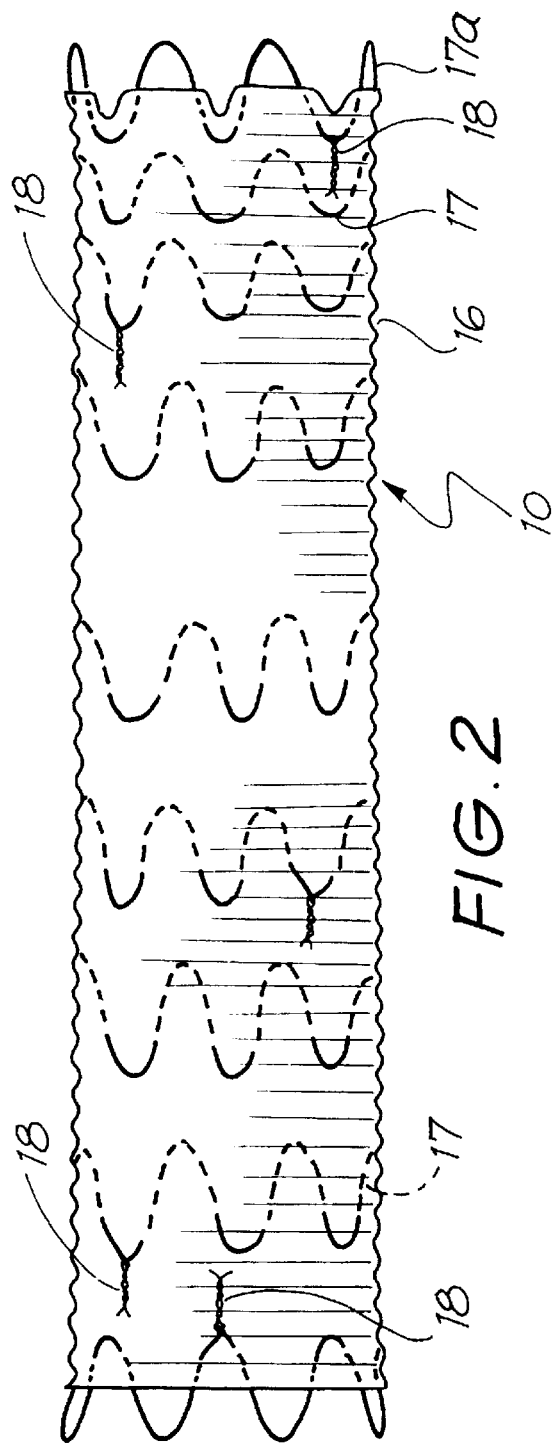
FIG. 2 is a side elevational view of one embodiment of a tubular intraluminal graft for use in the method described with reference to FIG. 1.
Figure 3:
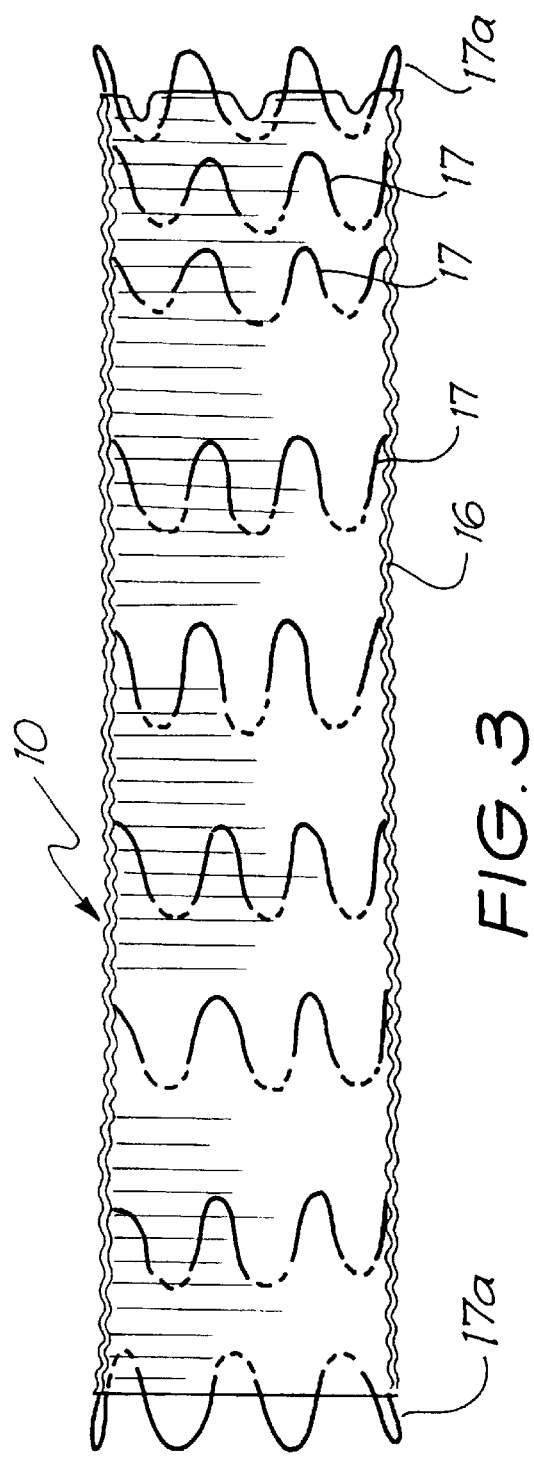
FIG. 3 is a longitudinal diametric sectional view through the intraluminal graft of FIG. 2.
Figure 5:
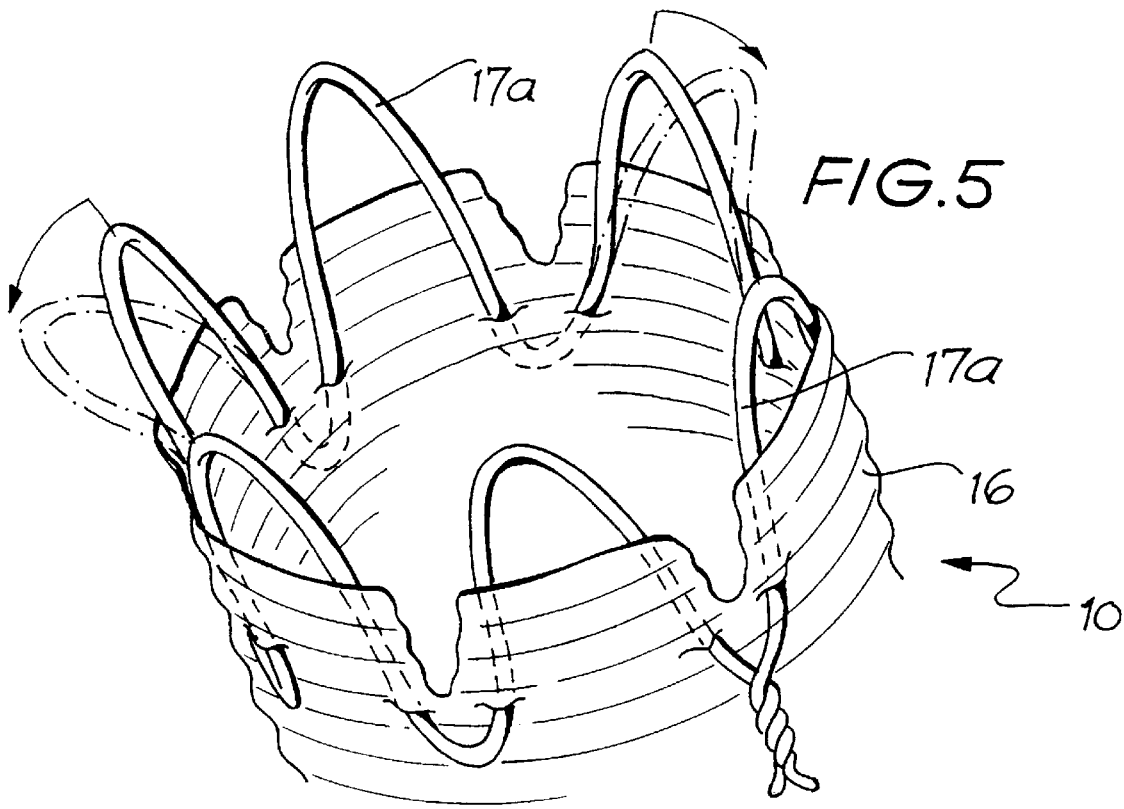
FIG. 5 is a detailed perspective view of the first end of the intraluminal graft of FIG. 4 showing how the alternate crests of the end wire of the graft are pushed radially outward during insertion of the graft.
Figure 4:
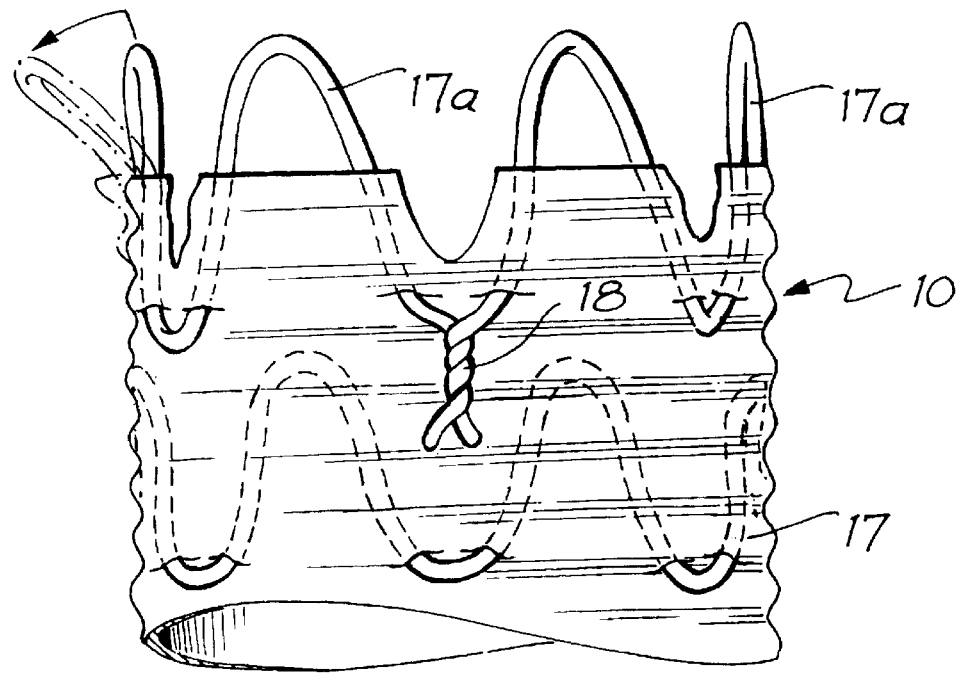
FIG. 4 is a detailed elevational view of one end of the intraluminal graft of FIG. 2.

A bifurcated or trouser graft comprising the three intraluminal grafts 10, 10a and 10b is adapted for insertion transfemorally into a patient to achieve bridging and occlusion of an aortic aneurysm extending at least into the left iliac artery. As is seen in FIG. 1 the aorta 11 is connected to the left and right iliac arteries 13, 12. The aortic aneurysm is located between the renal arteries 14, 15 and the iliac arteries 12, 13 with the aneurysm extending down at least the left iliac artery 13.

Each intraluminal graft (as is shown in FIGS. 2–5) can comprise a crimped tube 16 of woven polyester. Other materials could be utilised including polytetrafluoroethylene, polyurethane and composites thereof. The tube 16 is reinforced along its length by a number of separate and spaced apart stainless-steel wires 17 (each of which can have the depicted generally closed sinusoidal shape). The wires 17 are preferably as thin as possible and are typically 0.3 to 0.4 mm in diameter. The wires 17 are malleable and may be bent into any desired shape, ie they are not resilient to any substantial extent so that they have to be physically expanded into contact with the aorta rather than expanding by virtue of their own resilience. The wires 17 are each woven into the fabric of the tube 16 such that alternate crests of each wire 17 are outside the tube 16 with the remainder of that wire 17 inside the tube (except in the case of the endmost wires 17a as will be hereinafter described). The ends of each wire 17 are located outside the tube 16 and are twisted together to form a tail 18. The tails 18 of alternate wires 17 are bent to extend in opposite longitudinal directions along the outside surface of the tube 16. If desired, wires 17 may be formed in two parts with joining tails 18 on each side of the tube 16.

The endmost wires 17a overhang the respective ends of the tube 16 so that alternate crests of those wires extend longitudinally beyond the end of the tube 16. The endmost wires 17a preferably have an amplitude of about 6 mm and a wavelength such that between six and eight crests are spaced around the circumference of a 22 mm diameter graft. The next two adjacent wires 17 preferably are spaced as close as possible to the endmost wire 17a and respectively have amplitudes of 4 mm and 5 mm. These wires will typically have the same wavelength initially as the endmost wire 17a. Thereafter, throughout the graft the wires 17 are spaced at 15 mm intervals, have an amplitude of 6 mm, and have substantially the same initial wavelength as the endmost wire 17a.

As the aneurysm extends to, or beyond, the branching of the iliac arteries 12, 13 from the aorta 11 a single tubular graft is insufficient to bridge the aneurysm while maintaining blood flow to each of the iliac arteries 12 and 13. Rather than using a single tubular graft, in the present method three separate grafts 10, 10a and 10b are used. The downstream end of a first one of the grafts 10 (as depicted in FIG. 1) is provided with a bifurcation to form a pair of tubular graft extensions 19a, 19b of the graft 10. The tubular graft extensions 19a, 19b may be passively expandable by blood flow or actively expandable by balloon expansion or by spring self-expansion.

As is best depicted in FIGS. 9a–f, the graft portions 10a and 10b which are adapted to extend into the respective iliac arteries 12, 13 each have an upstream end having a common diameter. The upstream ends interlock with the respective extensions 19a, 19b of the graft 10 adapted to be positioned within the aorta 11. Preferably, this interlocking is achieved by balloon-expansion or spring self-expansion of the upstream ends such that there is a frictional engagement between the respective upstream ends and the extensions 19a, 19b.

In addition to having a straight cylindrical tube, the diameter of the downstream end 35 of the graft portions 10a and 10b can be provided in varying diameters so as to suit the diameter of the iliac artery into which graft portions 10a and 10b are being implanted.

Figure 9:
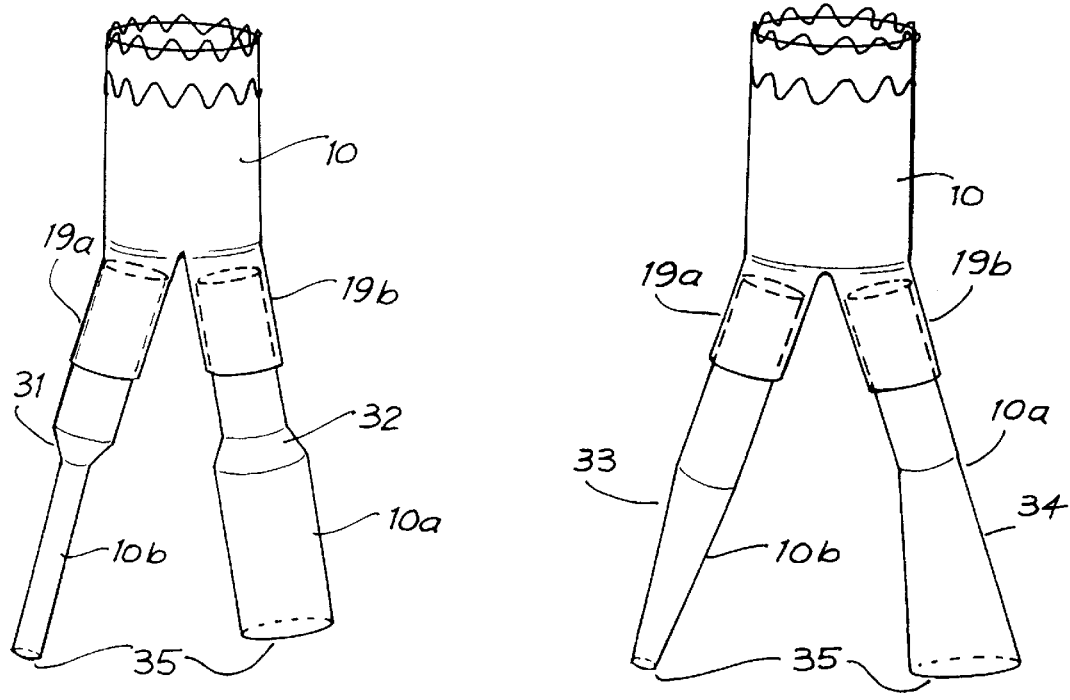
FIGS. 9a to 9f are simplified side elevational views of alternative intraluminal grafts for use in the method according to the present invention.
Figure 9:
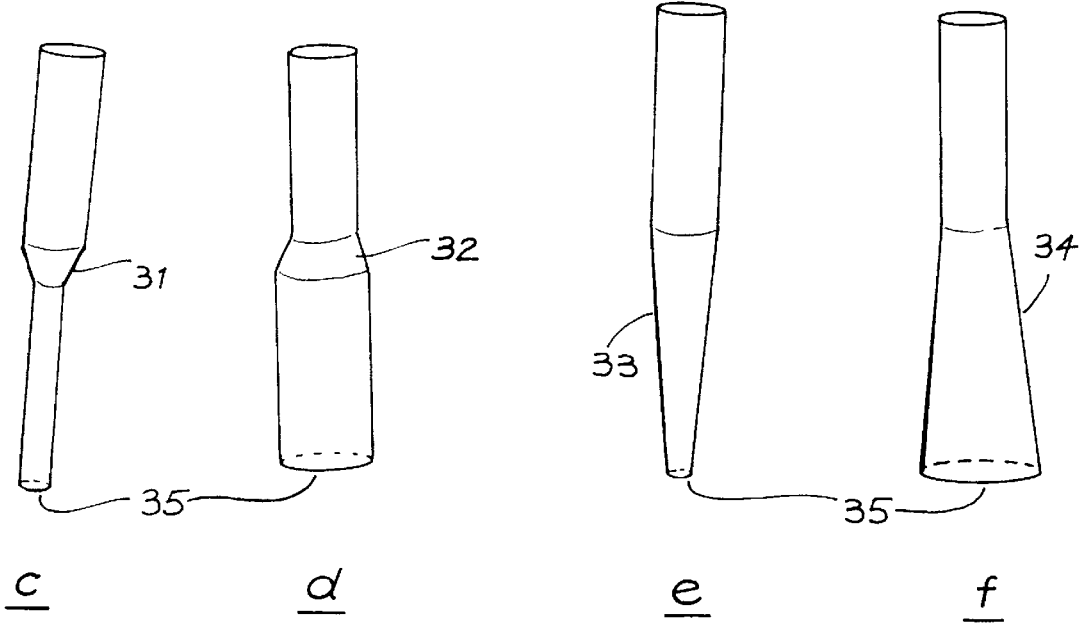

The change in diameter can be provided by a short step-down portion 31 (see FIG. 9c) or a step-up portion 32 (see FIG. 9d) or by a region of taper 33 and 34 extending along a length of the graft portion 10a or 10b (see FIGS. 9e and 9f).

One method for positioning the intraluminal graft will now be described with reference to FIGS. 7a–7i. In carrying out the method an incision or puncture is made to expose one of the femoral arteries (eg: ipsilateral), which flows from the corresponding iliac artery, and using the Seldinger needle technique a 0.035" diameter floppy tipped flexible guidewire is inserted into and through the femoral artery and then the iliac artery 12 into the aorta 11 such that it traverses the aneurysm. An 8 French haemostatic sheath is then introduced over the wire to control bleeding. An angiographic catheter is introduced to allow an angiogram to be taken of the patient to show the position of the renal arteries 14, 15 and other relevant anatomical structures in the patient.

Figure 7B:
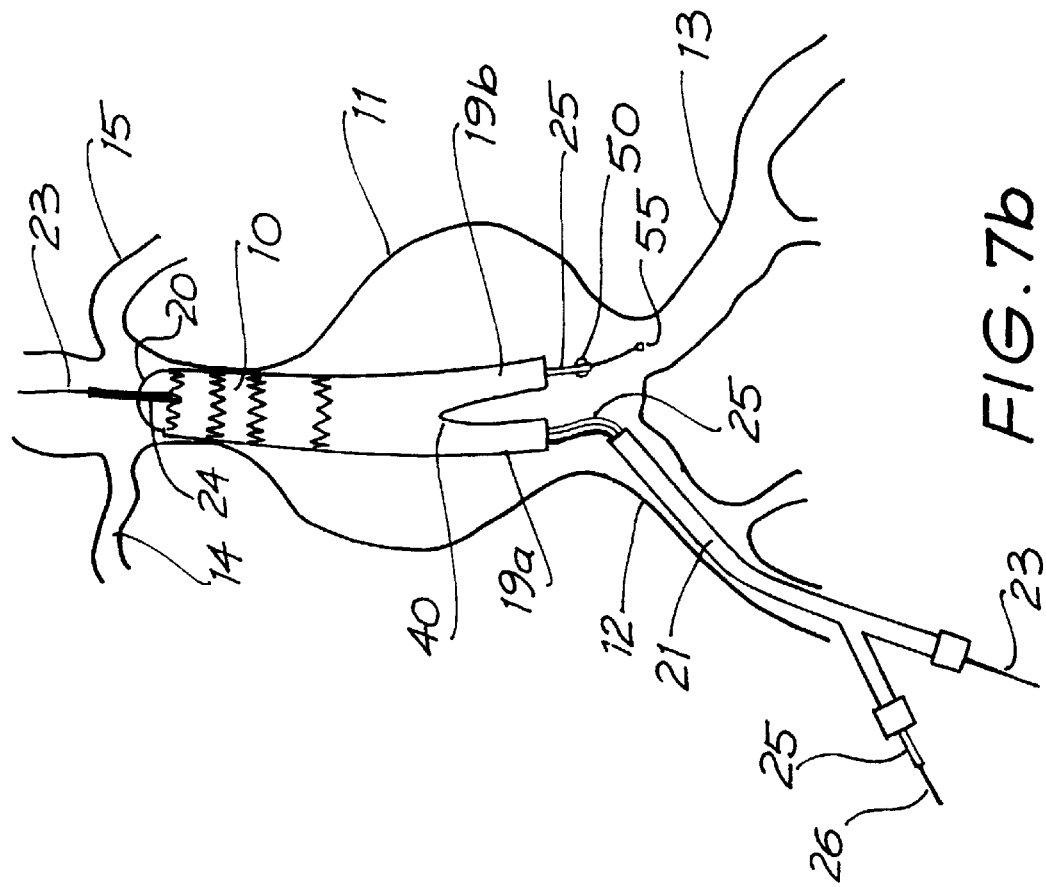
Figure 7A:
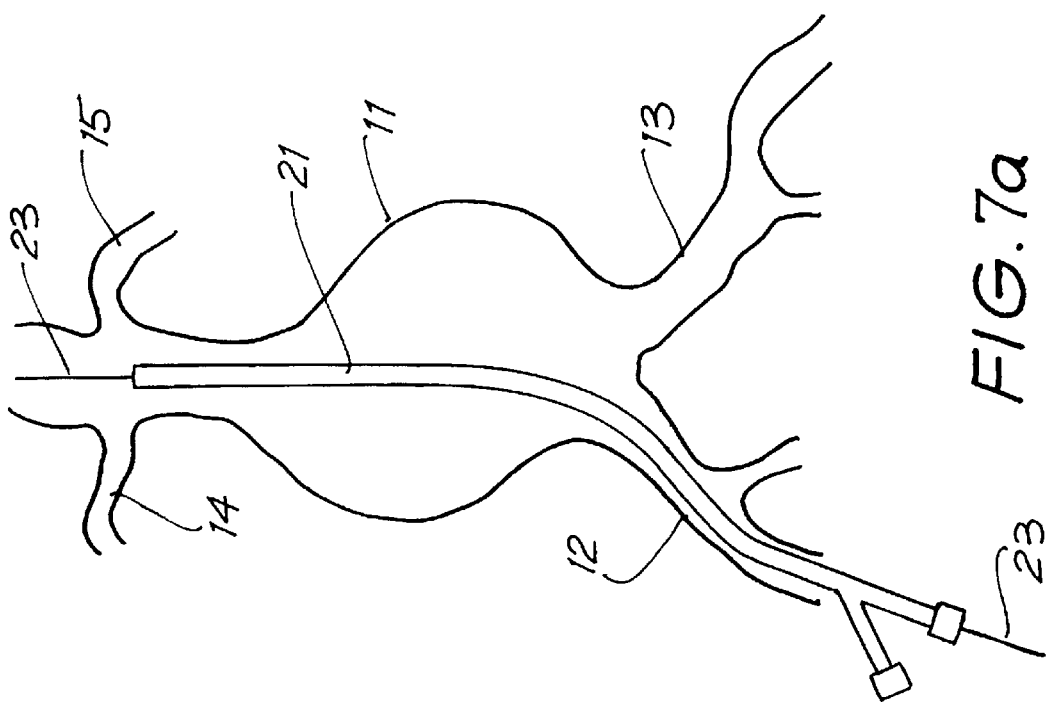
Figure 7D:
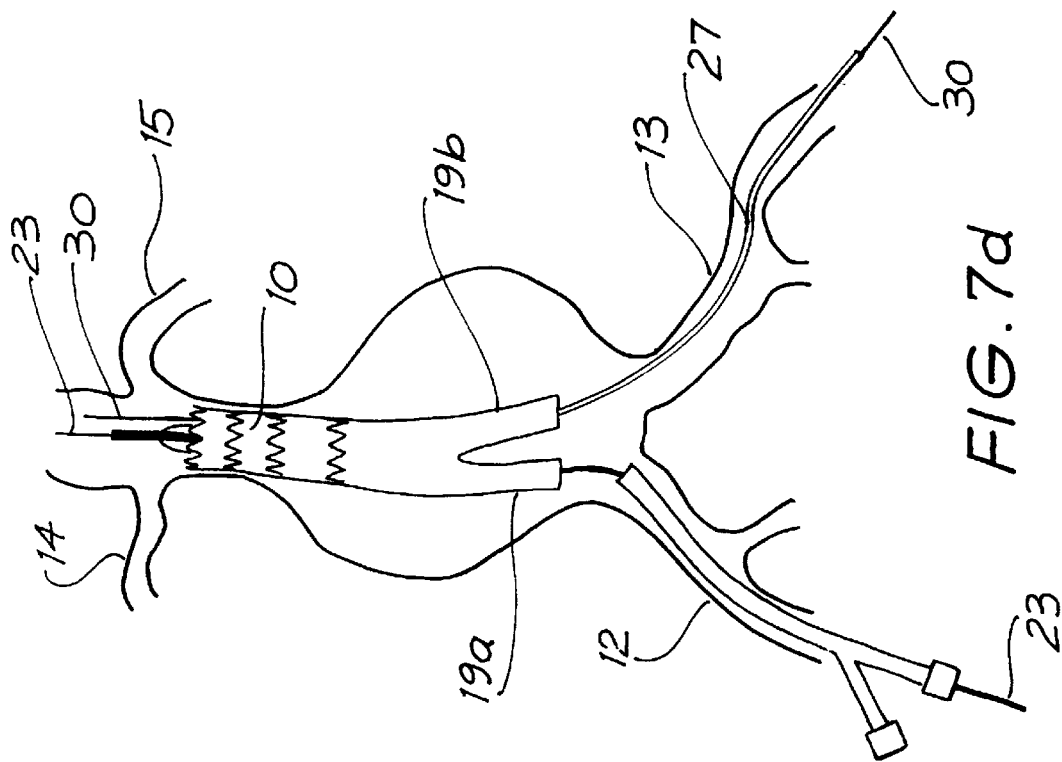

An Amplatz extra stiff (AES) guidewire 23 (0.035" diameter) is then passed through the angiographic catheter into the aorta 11 (see FIG. 7a). After withdrawal of the angiographic catheter, the stiff guidewire 23 is left in situ. A catheter sheath 21, preferably of 24 French, and trocar are then introduced into the aorta 11 over the stiff guidewire 23 (see FIG. 7a). A balloon catheter 24 is then introduced into the sheath 21.

Figure 6:
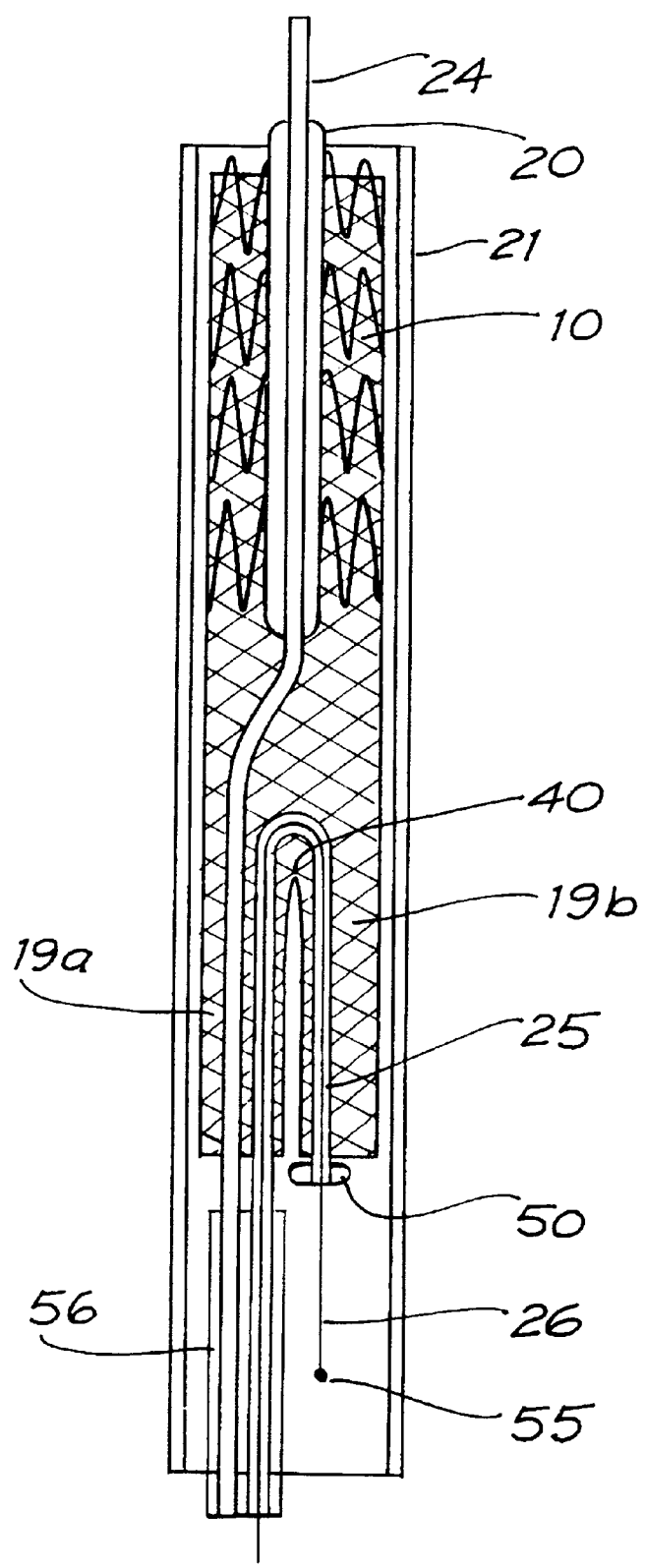
FIGS. 6 and 6a are vertical sectional views of two embodiments of possible bifurcated grafts mounted over delivery catheters for use in carrying out the present method.
Figure 6A:
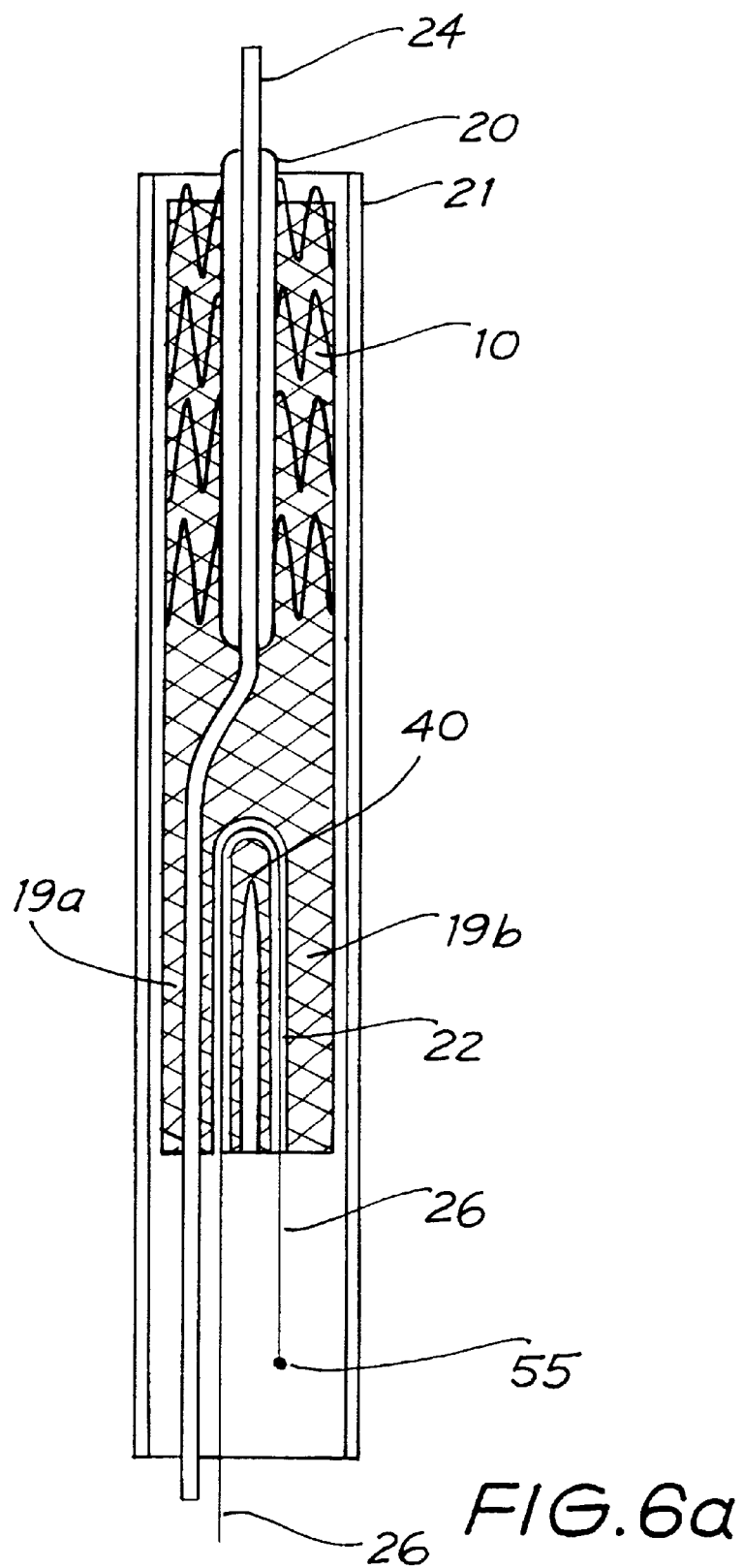

As is seen in FIG. 6, the balloon catheter 24 is a delivery catheter which is pre-packaged with a bifurcated graft 10, having the first and second tubular graft extensions 19a, 19b separated from a bifurcation point 40, and a thin catheter 25 containing a guidewire 26 extending in a first direction up through the first tubular graft extension 19a and then in a second different direction into the second tubular graft extension 19b.

The catheter 24 and thin catheter 25 can be linked together below the graft 10 in a common catheter sheath 56 which serves to better ensure correct positioning of the catheter 25 and guidewire 26 on placement of the graft 10 in the vessel. In addition to being slidable through the tubular graft extensions 19a,19b, the catheter 25 can be fixed in place in the graft 10 prior to insertion of the graft 10 into a vessel. The catheter 26 can be sutured, glued or woven into the body of the graft 10.

While the guidewire 26 is depicted in FIG. 6 inside a catheter 25, it can be readily envisaged that the guidewire 26 only could be disposed in the first and second tubular graft extensions 19a, 19b. In an alternative arrangement depicted in FIG. 6b, the guidewire 26 is positioned within a tubular channel 22 formed in the body of the graft 10. The channel 22 serves to ensure that the guidewire 26 remains placed in the desired position in the first and second tubular graft extensions 19a, 19b following packaging of the graft 10 about the balloon 20 and before placement of the balloon catheter 24 in the aorta 11.

When the balloon catheter 24 is positioned within the aorta 11 at the desired position the sheath 21 is partially withdrawn to free the graft 10 and the balloon 20 inflated (see FIG. 7b). The inflation of the balloon 20 of catheter 24 expands the upstream end of the first graft 10 and causes it to engage its upstream end against the aortic wall above the aneurysm but downstream of the renal arteries 14 and 15. The first graft 10 is of such a length that the tubular graft extensions 19a, 19b are disposed wholly within the aorta 11.

Figure 7C:
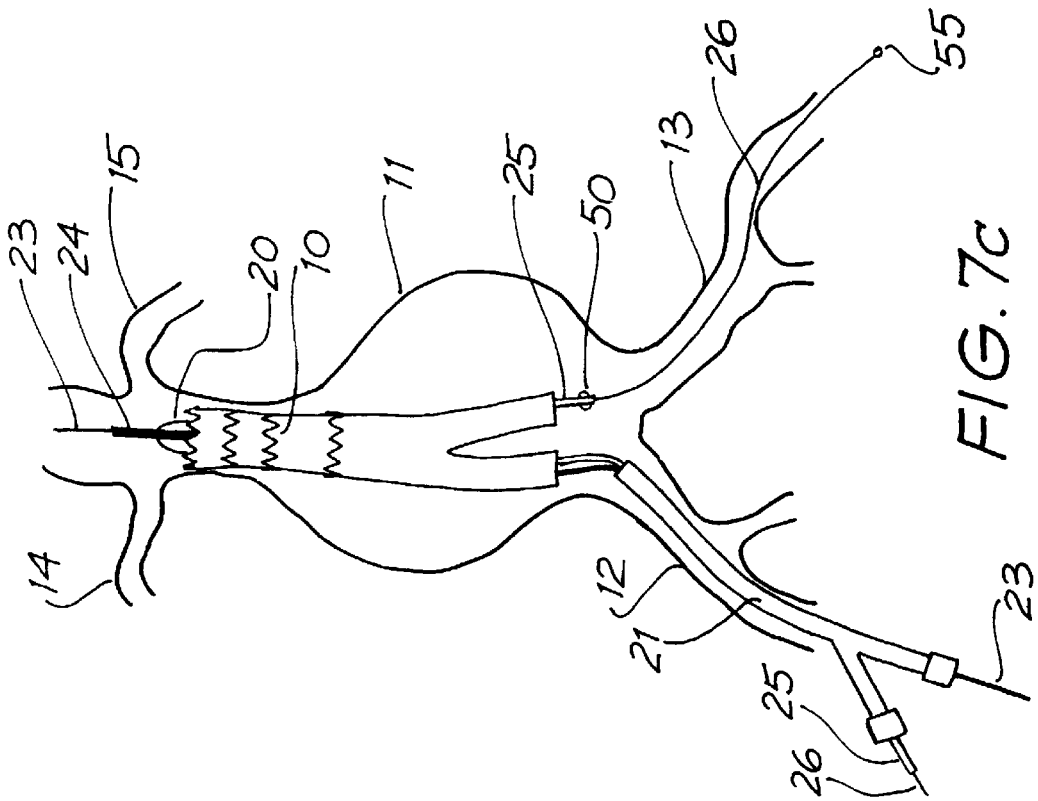
Figure 7H:
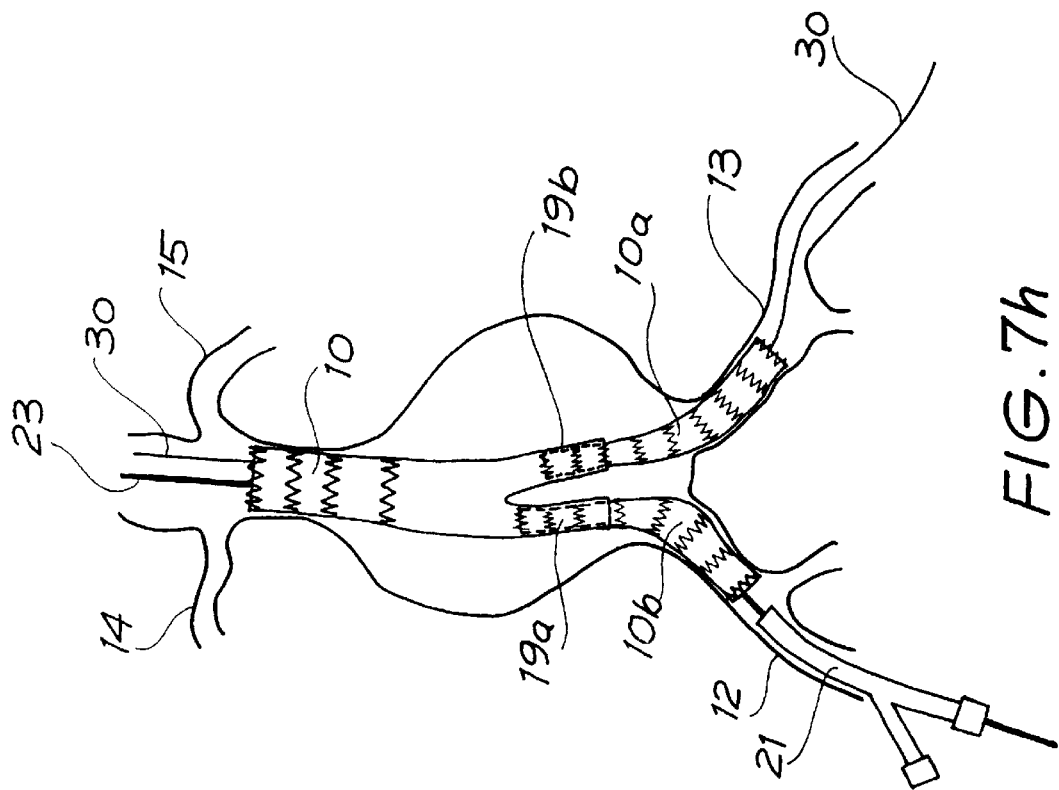
Figure 7G:
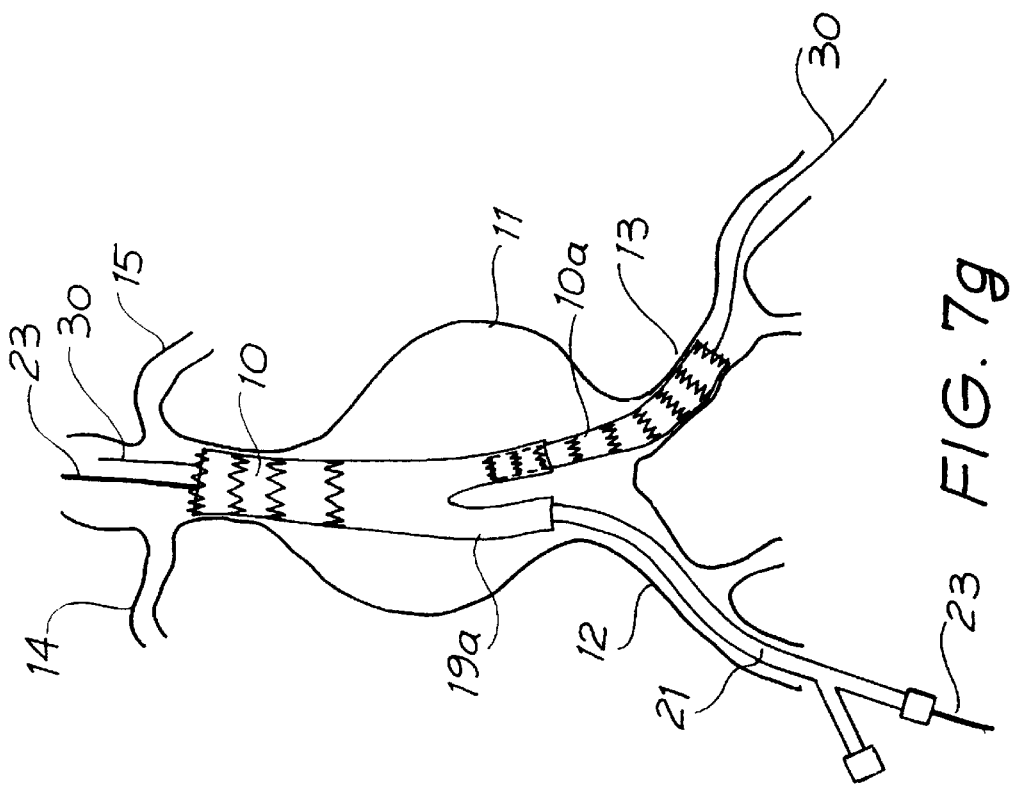

The balloon 20 is then deflated but the balloon catheter 24 is left in place for the time being (see FIG. 7c). Deflation of the balloon 20 will allow blood to flow down the graft 10 distending each of the tubular graft extensions 19a, 19b.

The thin catheter 25 is preferably 3 French and the guidewire 26 is preferably of a non-kinking material so that the guidewire 26 may be extended relative to the catheter 25 in a downstream direction (see FIG. 7c). The guidewire 26 is preferably comprised of a Nitinol core with a hydrophilic coating. In the method depicted in FIG. 7, the catheter 25 and guidewire 26 respectively have at their tip a small inflatable balloon 50,55. The details of the balloons 50,55 are depicted in more detail in FIGS. 6, 6b and 6c. The balloons 50,55 are inflated to help the catheter 25 and guidewire 26 to be carried and directed by blood flow into the contralateral iliac artery 13.

An enlarged view of the balloons 50,55 adjacent respectively the free ends of the catheter 25 and guidewire 26 is provided by FIGS. 6b and 6c. The catheter 25 has two lumens 52 and 53. The guidewire 26 passes through the first lumen 52. The end of the second lumen 53 is sealed and a small hole 51 has been formed in the outer surface of the catheter 25. A latex balloon 50 is annularly bonded to the outer surface of the catheter 25 at 50a. When the balloon 50 is to be inflated, liquid or gas is injected down the second lumen 53 such that it passes through the hole 51 and inflates the balloon 50. Similarly, the guidewire 26 has a lumen 54 down which air can be injected to inflate the balloon 55 disposed at the free end of the guidewire 26.

Figure 6D:
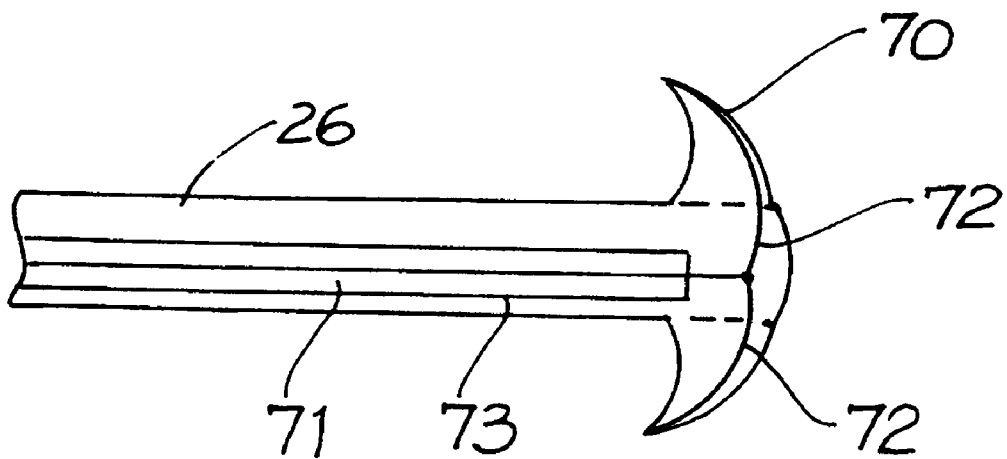
FIG. 6d is a simplified sectional view of a guidewire having an expandable umbrella adjacent its free end.
Figure 6E:
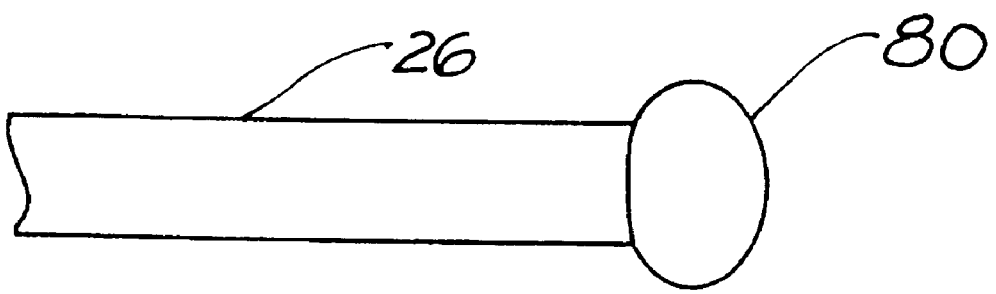
FIG. 6e is a simplified side elevational view of a guidewire having a solid bead at its free end.

While inflatable balloons are preferred, other expandable devices can be envisaged. For example, in an alternative embodiment, the balloons 50,55 on the catheter 25 and guidewire 26 could be replaced by an expandable umbrella. An example of a type of umbrella that could be utilised is depicted in FIG. 6d. Disposed at the free end of the guidewire 26 is an umbrella 70. The umbrella 70, which is depicted in the expanded configuration in FIG. 6d, is expanded by a wire 71 extending through a lumen 73 in the guidewire 26. The wire 71 is attached to stays 72 so that on retraction of wire 71 the stays 72 articulate to expand the umbrella 70. While the umbrella 70 is on the guidewire 26 it can be readily envisaged that a similar arrangement could be utilised on the catheter 25. In a further alternative, the balloon 55 on the guidewire 26 can be replaced by a small solid bead 80 of material such as epoxy resin or titanium as depicted in FIG. 6e. The bead 80 preferably has a larger profile than the guidewire 26.

In certain applications it is desirable once the catheter 25 is in a desired position in a vessel to further expand the balloon 50 at the free end of the catheter until the balloon 50 engages the wall of the vessel and holds the catheter 25 in a desired position within the vessel to provide additional anchorage during passage of the guidewire 26 through the vessel.

Once the guidewire 26 is correctly placed in the contralateral femoral artery a cut down is effected to that femoral artery which is cross-clamped and an arteriotoiny effected. If the guidewire 26 has been guided fully into the contralateral femoral artery, the guidewire 26 is simply recovered by drawing the guidewire through the incision or puncture made in the artery. If the guidewire 26 has not been guided fully into the contralateral femoral artery, a snare or similar device can be introduced through the contralateral femoral artery to grab the guidewire 26 and draw it back to the incision or puncture site for retrieval. Once the guidewire 26 is retrieved, the thin catheter 25 is then withdrawn via the ipsilateral side and another catheter 27 fed through the contralateral femoral artery up the guidewire 26 until it is within the first graft 10 and reaches at least to the top of the second tubular graft extension 19b (see FIG. 7d). The thin guidewire 26 is then withdrawn and a thicker guidewire 30 inserted through the contralateral femoral artery into the catheter 27. The catheter 27 is then removed and a catheter sheath 21a, preferably of 24 French, and trocar are introduced over the stiff guidewire 30 (see FIG. 7e).

Prior to extending the guidewire 26 into the contralateral iliac and femoral arteries, a catheter sheath (that can be similar to catheter sheath 21) can be extended upstream through the contralateral femoral and iliac arteries to reduce any tortuosity that may be present in these arteries and so facilitate guiding of the guidewire 26 therethrough.

Figure 10:
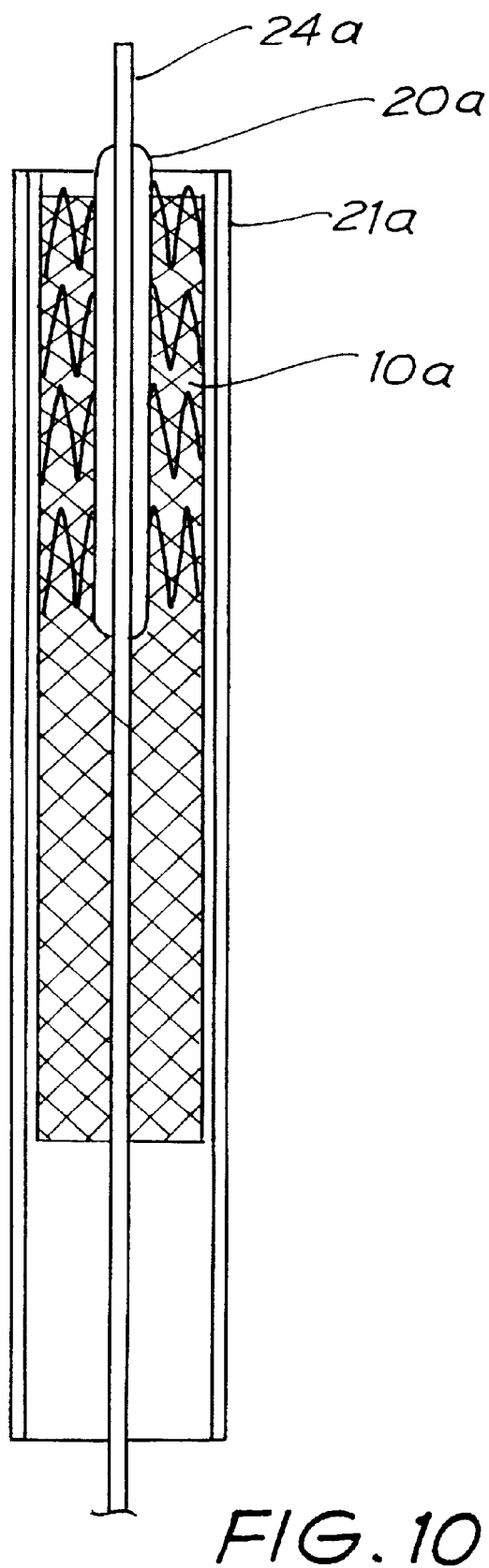
FIG. 10 is a vertical sectional view of one embodiment of a tubular graft mounted over a delivery catheter that can be used in carrying out the present invention.

A second balloon catheter 24a, such as depicted in FIG. 10, on which is packaged a second tubular graft 10a, is then introduced through catheter sheath 21a until its upper end is well within the second tubular graft extension 19b and within the iliac artery 13 at its lower end. The balloon 20a on the catheter 24a is inflated such that the upper end of graft 10a is frictionally engaged with the second tubular graft extension 19b (see FIG. 7f). The inflation of the balloon 20a on the catheter 24a supports the graft 10a during the withdrawal of the first balloon catheter 24 through the ipsilateral artery 12. The balloon 20a on the catheter 24a is then deflated and the catheter 24a maintained in place to provide continued support for the grafts 10, 10a in the aorta while the third graft 10b is positioned.

The catheter sheath 21a is then removed (see FIGS. 7f and 7g) and a third balloon catheter on which is packaged a tubular graft 10b (the third balloon catheter lob can be identical to that depicted in FIG. 10) is introduced into the sheath 21 on guidewire 23. It is advanced until its upstream end is within the first tubular graft extensions 19a and, following partial withdrawal of the sheath 21, is then deployed. The third graft 10b positioned on the third balloon catheter is thus urged at its upstream end into contact with first tubular graft extension 19a and at its downstream end into contact with the right iliac artery 12 (see FIG. 7h).

Figure 7I:
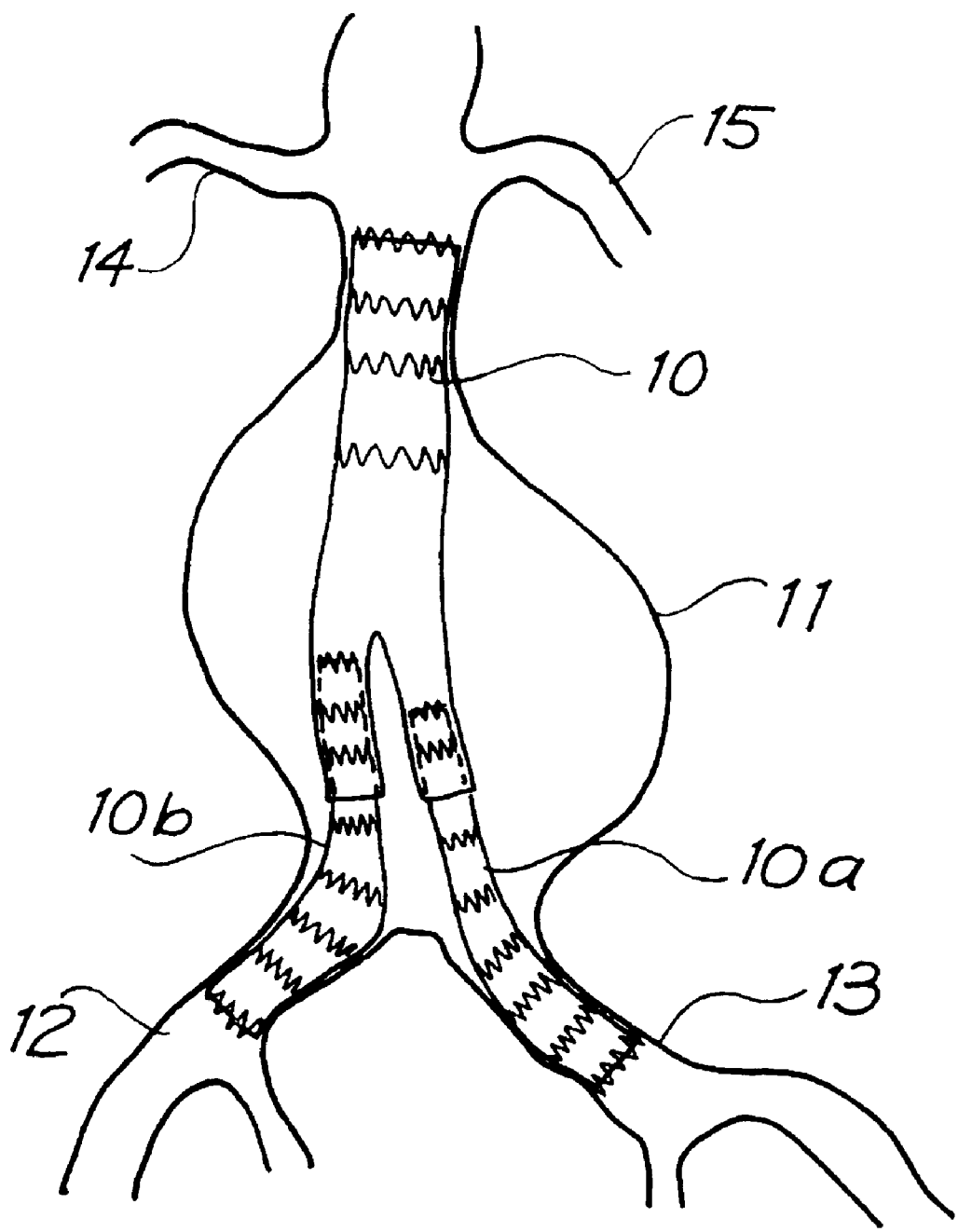

The stiff guidewires 23 and 30 are now withdrawn and the contralateral incision or puncture sutured. A second angiographic examination now takes place and if the grafts 10, 10a and 10b are correctly placed and functioning, the haemostatic sheath 21 is withdrawn and the right femoral artery closed by suture. The result is a functioning trouser graft bridging an aneurysm as is depicted in FIG. 7i.

A different method for positioning the intraluminal graft will now be described with reference to FIGS. 8a–8e, where like features have the same reference numerals as the earlier Figures. As with the method depicted in FIG. 7, in carrying out the method an incision or puncture is made to expose one of the femoral arteries (eg: ipsilateral), which flows from the corresponding iliac artery 12, and using the Seldinger needle technique a 0.035" diameter floppy tipped flexible guidewire is inserted into and through the femoral artery and then the iliac artery 12 into the aorta 11 such that it traverses the aneurysm. An 8 French haemostatic sheath is then introduced over the wire to control bleeding. An angiographic catheter is introduced to allow an angiogram to be taken of the patient to show the position of the renal arteries 14, 15 and other relevant anatomical structures in the patient.

Figure 8B:
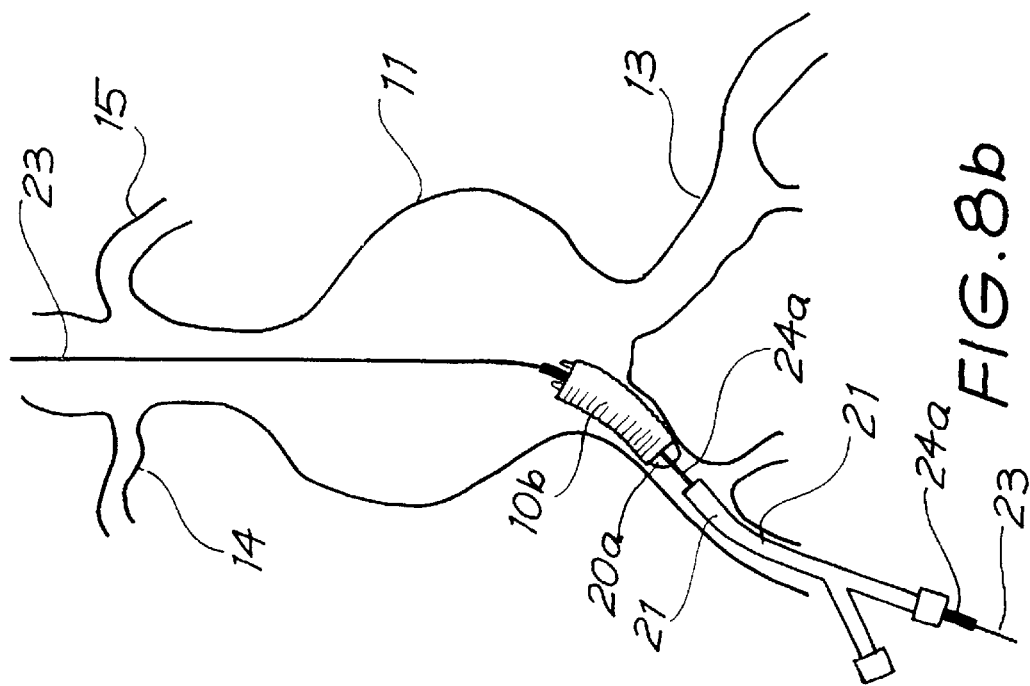
FIG. 8a to 8e show the stages of carrying out another method according to the present invention.
Figure 8A:
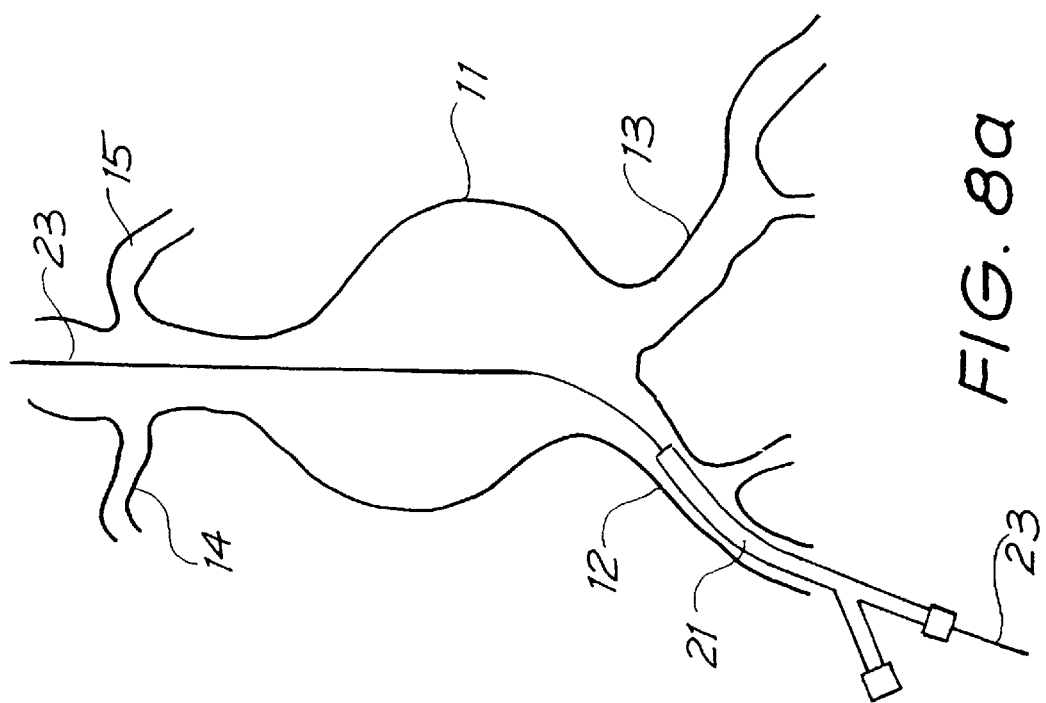
Figure 8D:
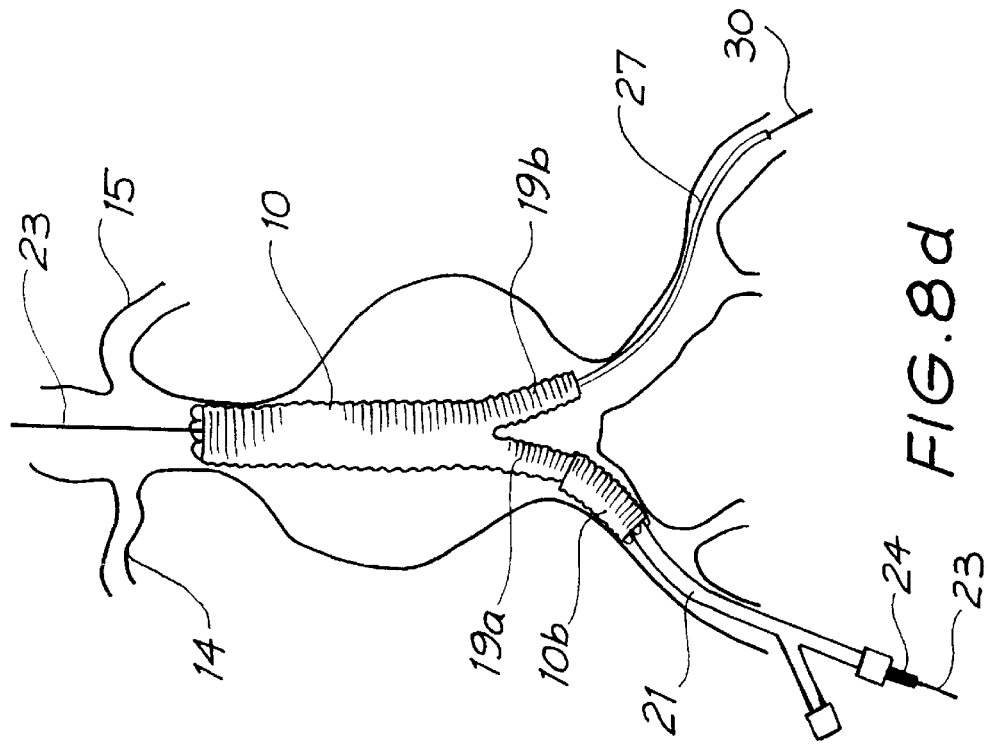
Figure 8C:
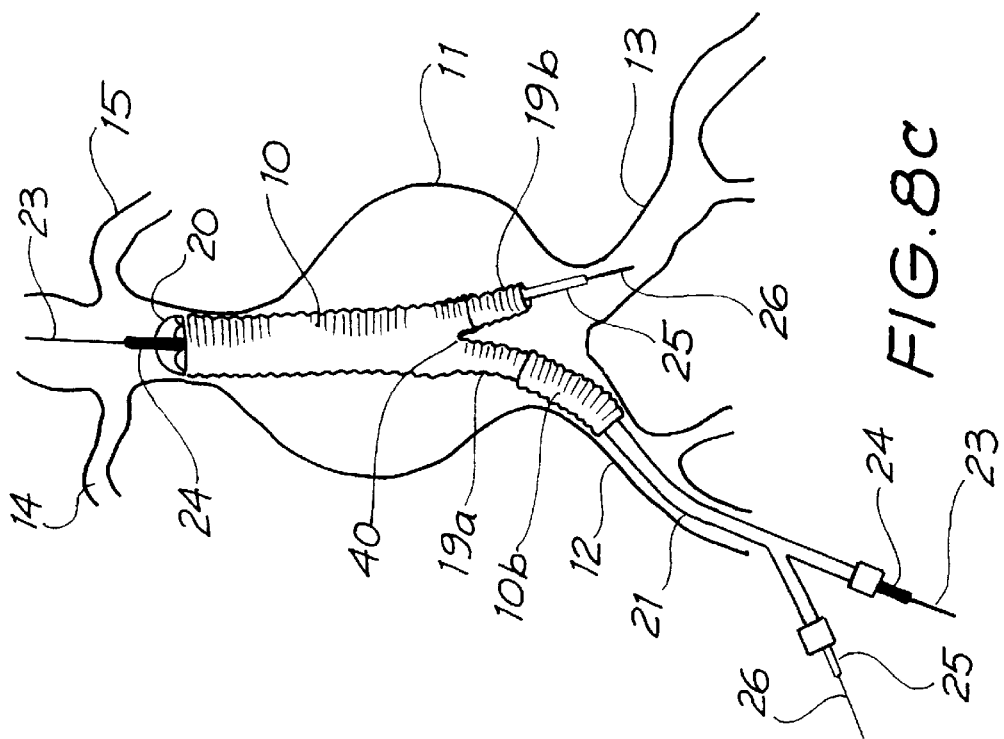
Figure 8E:
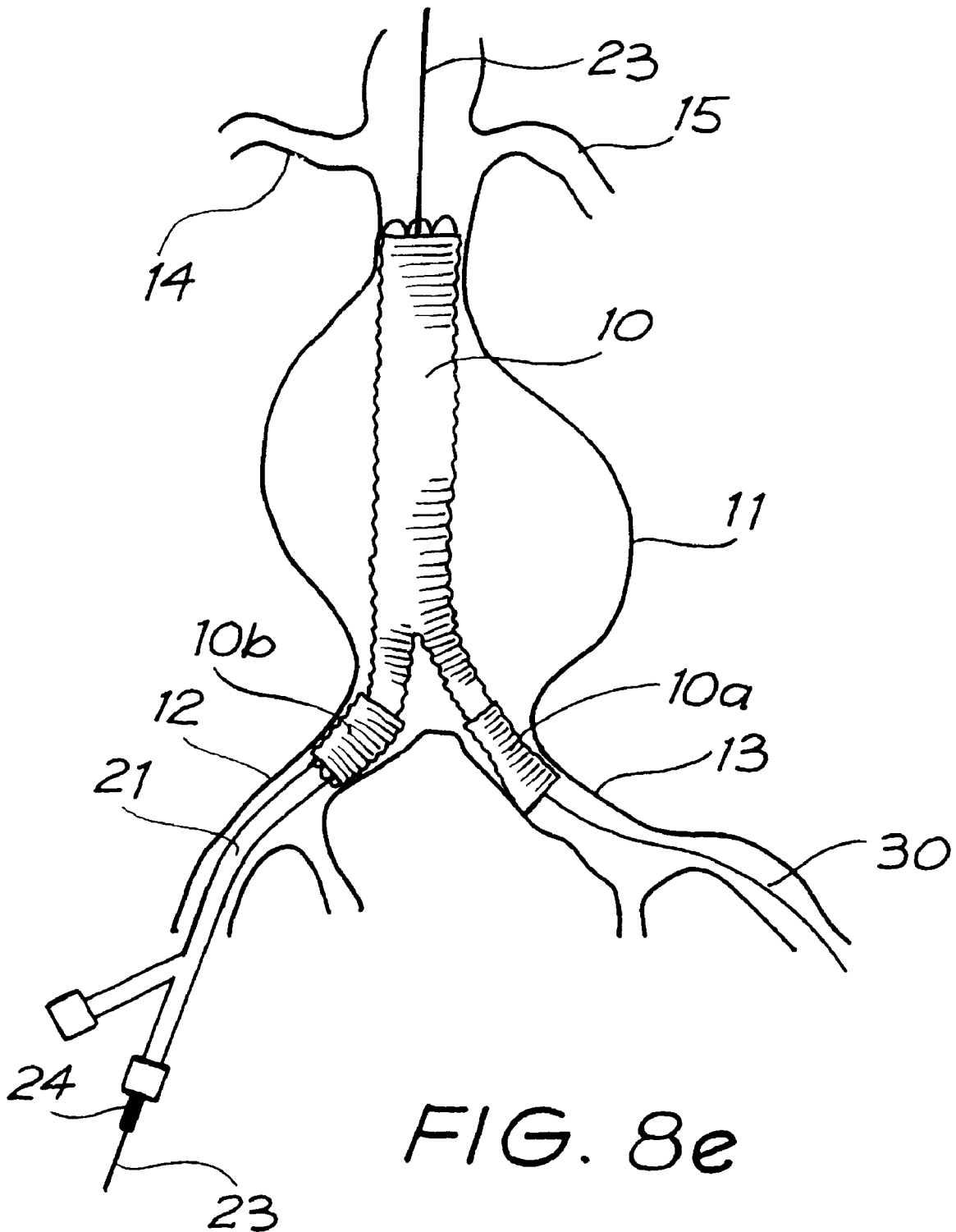

An Amplatz extra stiff (AES) guidewire 23 (0.035" diameter) is then passed through the angiographic catheter into the aorta 11 (see FIG. 8a). After withdrawal of the angiographic catheter, the stiff guidewire 23 is left in situ. A catheter sheath 21, preferably of 24 French, and trocar are then introduced into the iliac artery 12 over the stiff guidewire 23 (see FIG. 8a). A balloon catheter 24a (such as is depicted in FIG. 10) is then introduced into the sheath 21. The balloon catheter 24a in this case is pre-packaged with a tubular graft 10b. When the catheter 24a is positioned within the iliac artery 12, the catheter sheath 21 is partially withdrawn to free the graft 10b and the balloon 20a is then inflated (see FIG. 8b). The inflation of the balloon 20a on the catheter 24a expands the downstream end of the graft 10b and causes it to engage against the wall of the iliac artery 12 below the aneurysm. The balloon 20a is then deflated and the catheter 24a withdrawn.

The catheter sheath 21 is then passed through the graft 10b and introduced into the aorta 11 over the stiff guidewire 23. The balloon catheter 24 (such as depicted in FIG. 6) is then introduced into the sheath 21. The balloon catheter 24 is pre-packaged with a bifurcated graft 10, having a bifurcation point 40, two tubular graft extensions 19a, 19b, a thin catheter 25 and a guidewire 26. The balloon catheter 24 with graft 10 carried or placed thereon is passed through the tubular graft lob and positioned within the aorta 11. Once the balloon catheter 24 is positioned in the aorta 11, the catheter sheath 21 is partially withdrawn to free the graft 10 and allow for inflation of the balloon 20 on the catheter 24. The inflation of the balloon 20 expands the upstream end of the of the graft 10 against the aortic wall above the aneurysm but downstream of the renal arteries 14,15 (see FIG. 8c). The tubular graft extension 19a of graft 10 that extends into graft 10b when used in this method is longer than tubular graft extension 19b and this ensures that when the balloon catheter 24 is appropriately positioned in the aorta 11, graft extension 19a overlaps with graft 10b and tubular graft extension 19b is free of graft 10b. The balloon 20 is then deflated and partially withdrawn to the upstream end of the tubular graft 10b where it is reinflated to expand the tubular graft extension 19a into contact with the overlapping graft 10b and so form a fluid conveying engagement between the grafts 10 and 10b.

The thin catheter 25 and guidewire 26 can then be deployed in a downstream direction in a manner similar to that described above with reference to FIG. 7. Once the guidewire 26 is correctly placed in the contralateral femoral artery a cut down is effected to the femoral artery which is cross-clamped and an arteriotomy effected. The free end of the guidewire 26 is then retrieved as already described at which point the thin catheter 25 can be withdrawn through the ipsilateral side. Another catheter 27 is then fed through the contralateral femoral artery up the guidewire 26 until it is within the first graft 10 and reaches at least to the top of the graft extension 19b. The thin guidewire 26 is then withdrawn and a thicker guidewire 30 inserted through the contralateral femoral artery into the catheter 27 (see FIG. 8d). The catheter 27 is then removed and a catheter sheath 21a, preferably of 24 French, and trocar are introduced over the stiff guidewire 30 in a manner similar to that described with reference to FIG. 7.

A third balloon catheter (having the features of the catheter depicted in FIG. 10), on which is packaged a second tubular graft 10a, is then introduced through catheter sheath 21a until its upper end is well within tubular graft extension 19b. The balloon on the third balloon catheter is then inflated such that the upper end of graft 10a is frictionally engaged with graft extension 19b. The balloon on the third catheter is then deflated and the balloon catheter withdrawn through the contralateral femoral artery (see FIG. 8e).

The balloon 20 on catheter 24 which is still inflated at the upstream end of the graft 10b is then deflated and the balloon catheter 24a fully withdrawn. The catheter sheath 21a, the guidewire 23, and guidewire 30 are then removed and the contralateral incision or puncture sutured. As with the earlier described method, a second angiographic examination now takes place and if the grafts 10, 10a and 10b are correctly placed and functioning, the haemostatic sheath 21 is withdrawn and the ipsilateral femoral artery closed by suture. The result is a functioning trouser graft similar to that depicted in FIG. 7i.

A further modification of the method for placing the grafts 10, 10a and 10b in a branching vessel depicted in FIG. 8a–8e, can involve, following placement of the tubular graft 10b in the right iliac artery 12, the introduction of the delivery catheter 24 carrying graft 10 into the aorta 11 through the left iliac artery 13. Once the graft 10 is positioned where desired and appropriate connection is made between grafts 10 and 10a, the graft 20b can then be introduced through the left iliac artery 13 and appropriately positioned to complete the placement of the trouser graft.

The various methods of operation may be carried out using a general anaesthetic, an epidural anaesthetic or, in suitable cases, using only a local anaesthetic.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for positioning a bifurcated graft across a distended region of a main vessel adjacent a bifurcation of the main vessel into an ipsilateral vessel and a contralateral vessel, the method comprising:

introducing a catheter pre-packaged with a bifurcated graft therein into the ipsilateral vessel and then into the main vessel to a point beyond the distended region, the bifurcated graft having a tubular main portion branching into two tubular extensions at a bifurcation point, namely, an ipsilateral extension and a contralateral extension;

deploying the bifurcated graft from within the catheter so that the tubular main portion contacts the walls of the main vessel at a point beyond the distended region and the tubular extensions are located within the distended region and pointing toward respective ipsilateral and contralateral vessels;

delivering a flexible guidewire through the ipsilateral vessel and ipsilateral extension and causing it to deflect around the bifurcation point into the contralateral extension and then into contralateral vessel;

deploying a tubular contralateral graft through the contralateral vessel using the flexible guidewire;

engaging a first end of the contralateral graft with the contralateral extension;

engaging a second end of the contralateral graft with the contralateral vessel;

deploying a tubular ipsilateral graft through the ipsilateral vessel;

engaging a first end of the ipsilateral graft with the ipsilateral extension; and engaging a second end of the ipsilateral graft with the ipsilateral vessel.

2. The method of claim 1, wherein the step of deploying the contralateral graft includes:

a. using the flexible guidewire as a locator within the contralateral extension of the bifurcated graft to deliver a stiff guidewire into the contralateral extension from the contralateral vessel; and b. passing the contralateral graft over the stiff guidewire into the contralateral extension.

3. The method of claim 2, further including:

a. passing an exchange catheter from the contralateral vessel over the flexible guidewire until the exchange catheter is within the contralateral extension;

b. removing the flexible guidewire from within the exchange catheter;

c. passing the stiff guidewire from the contralateral vessel through the exchange catheter until the stiff guidewire is within the contralateral extension; and d. removing the exchange catheter.

4. The method of claim 2, wherein the step of passing the contralateral graft over the stiff guidewire into the contralateral extension comprises:

a. passing a sheath over the stiff guidewire; and b. passing a catheter having the contralateral graft packaged thereon through the sheath and into the contralateral extension.

5. The method of claim 4, wherein the step of engaging a first end of the contralateral graft with the contralateral extension includes:

a. balloon expanding the first end of the contralateral graft into engagement with the contralateral extension using a balloon on the catheter on which the contralateral graft is packaged.

6. The method of claim 1, wherein the step of deploying the ipsilateral graft through the ipsilateral vessel and engaging the first end of the ipsilateral graft with the ipsilateral extension includes:

a. passing a stiff guidewire from the ipsilateral vessel and into the ipsilateral extension;

b. passing a sheath over the stiff guidewire;

c. passing a catheter having the contralateral graft packaged thereon through the sheath and into the ipsilateral extension; and d. balloon expanding the first end of the ipsilateral graft into engagement with the ipsilateral extension using a balloon on the catheter on which the ipsilateral graft is packaged.

7. The method of claim 1, wherein the ipsilateral and contralateral vessels are located downstream in the blood flow from the main vessel, and wherein the step of delivering a flexible guidewire includes the step of deploying means on the end of the flexible guidewire for helping the bloodstream to carry the end of the guidewire through the contralateral vessel.

8. The method of claim 7, wherein step of deploying means on the end of the flexible guidewire includes inflating a balloon located on the end of the guidewire.

9. The method of claim 7, wherein step of deploying means on the end of the flexible guidewire includes expanding an umbrella-like structure located on the end of the guidewire.

10. A bifurcated graft assembly for bridging a distended region of a main vessel adjacent a bifurcation of the main vessel into two branching vessels, the assembly comprising:

a. a bifurcated graft having a tubular main portion branching into two tubular extensions at a bifurcation point, the bifurcated graft including a graft body reinforced with a plurality of separate and spaced apart wires in the main portion and tubular extensions, wherein at least the wires in the main portion are woven through the graft body, and at least a wire at the ends of the tubular extensions is self-expanding; and b. at least one tubular graft sized to connect between one of the tubular extensions of the bifurcated graft and the respective branching vessel, the tubular graft having a graft body reinforced with wires, wherein a wire in a first end of the tubular graft is balloon-expandable, the first end of the tubular graft being overlapped within and being capable of outward expansion into frictional engagement with the end of the tubular extension to form the graft assembly.

11. The bifurcated graft assembly of claim 10, wherein there are a pair of the tubular grafts sized to connect between both tubular extensions of the bifurcated graft and the respective branching vessels, the tubular grafts each having a graft body reinforced with wires, wherein a wire in a first end of each of the tubular grafts is balloon-expandable, the first end of each of the tubular grafts being overlapped within and being capable of outward expansion into frictional engagement with the ends of the tubular extensions to form the graft assembly.

12. The bifurcated graft assembly of claim 10, wherein each of the wires woven through the graft body has a generally closed sinusoidal shape with adjacent crests extending in opposite directions, wherein the wires are generally disposed inside the graft body with alternate crests woven through to the outside of the graft body.

13. The bifurcated graft assembly of claim 10, wherein each of the wires woven through the graft body has a generally closed sinusoidal shape with an amplitude.

14. The bifurcated graft assembly of claim 10, wherein at least one of the wires in the main portion has a different amplitude than the other wires.

15. The bifurcated graft assembly of claim 14, wherein the wire located closest to the end of the main portion has a larger amplitude than the other wires in the main portion.

16. The bifurcated graft assembly of claim 10, wherein the wires in the main portion of the bifurcated graft are balloon-expandable.

17. A bifurcated graft assembly for bridging a distended region of a main vessel adjacent a bifurcation of the main vessel into two branching vessels, the assembly comprising:

a. a bifurcated graft having a tubular main portion branching into two tubular extensions at a bifurcation point, the bifurcated graft including a bifurcated graft body reinforced with a plurality of separate and spaced apart wires in the main portion and tubular extensions each of which has a generally closed sinusoidal shape, at least one wire at the ends of each of the tubular extensions is self-expanding, a first wire being located adjacent to the end of the main portion of the bifurcated graft body such that alternate apices of the first wire projects beyond at least part of the end; and b. at least one tubular graft sized to connect between one of the tubular extensions of the bifurcated graft and the respective branching vessel, the tubular graft having a graft body reinforced with wires, wherein a wire in a first end of the tubular graft is balloon-expandable, the first end of the tubular graft being overlapped within and being capable of outward expansion into frictional engagement with the end of the tubular extension to form the graft assembly.

18. The bifurcated graft assembly of claim 17, wherein there are a pair of the tubular grafts sized to connect between both tubular extensions of the bifurcated graft and the respective branching vessels, the tubular grafts each having a graft body reinforced with wires, wherein a wire in a first end of each of the tubular grafts is balloon-expandable, the first end of each of the tubular grafts being overlapped within and being capable of outward expansion into frictional engagement with the ends of the tubular extensions to form the graft assembly.

19. The bifurcated graft assembly of claim 17, wherein the wires in the main portion of the bifurcated graft are balloon-expandable.

20. The bifurcated graft assembly of claim 17, wherein the end of the main portion of the bifurcated graft body includes an edge which is scalloped between each projecting apex of the first wire.

21. The bifurcated graft assembly of claim 17, wherein at least the wires in the main portion are woven through the graft body, wherein the wires are generally disposed inside the graft body with alternate apices woven through to the outside of the graft body.

22. The bifurcated graft assembly of claim 1, wherein each of the wires woven through the graft body has a generally closed sinusoidal shape with an amplitude.

23. The bifurcated graft assembly of claim 17, wherein at least one of the wires in the main portion has a different amplitude than the other wires.

24. The bifurcated graft assembly of claim 23, wherein the first wire has a larger amplitude than the other wires in the main portion.

* * * * *

UNITED STATES PATENT AND TRADEMARK OFFICE
CERTIFICATE OF CORRECTION

PATENT NO.     : 6,099,558
DATED          : August 8, 2000
INVENTOR(S)    : Geoffrey H. White and Weiyun Yu Page 1 of 1

It is certified that error appears in the above-identified patent and that said Letters Patent is hereby corrected as shown below:

<u>Title page,</u>
Item [73], Assignee, please delete "Edwards Lifesciences Corp." and insert the following:
-- Endogad Research PTY Limited --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,099,558  
APPLICATION NO. : 09/068587  
DATED : August 8, 2000  
INVENTOR(S) : White et al.

Page 1 of 1

It is certified that error appears in the above-identified patent and that said Letters Patent is hereby corrected as shown below:

On Title Page should read  
Item 22  
PCT Filed: November 11, 1996

Signed and Sealed this

Third Day of June, 2008

JON W. DUDAS  
*Director of the United States Patent and Trademark Office*